(12) United States Patent
Tyler

(10) Patent No.: US 6,691,046 B2
(45) Date of Patent: Feb. 10, 2004

(54) METHOD AND APPARATUS FOR IDENTIFYING UNKNOWN COMPOUNDS IN COMPLEX CHEMICAL MIXTURES USING MASS SPECTROMETRY AND MASS DIFFERENTIAL ANALYSIS

(75) Inventor: Andrew N. Tyler, Reading, MA (US)

(73) Assignee: NeoGenesis Drug Discovery, Inc., Cambridge, MA (US)

( * ) Notice: Subject to any disclaimer, the term of this patent is extended or adjusted under 35 U.S.C. 154(b) by 0 days.

(21) Appl. No.: 09/852,596

(22) Filed: May 10, 2001

(65) Prior Publication Data

US 2002/0169567 A1 Nov. 14, 2002

(51) Int. Cl.$^7$ ................................................ G06F 17/00
(52) U.S. Cl. .............................. 702/27; 702/32; 703/12
(58) Field of Search .............................. 702/27–32, 19, 702/22, 23, 25, 183, FOR 115–FOR 121, FOR 131, FOR 134, FOR 140, FOR 170; 356/302, 303; 422/62, 67, 68.1; 436/2; 435/6; 564/133; 250/281, 282, 288; 382/128; 703/2, 11, 12; 700/266, 268

(56) References Cited

U.S. PATENT DOCUMENTS 6,008,490 A * 12/1999 Kato .......................... 250/282
6,147,344 A * 11/2000 Annis et al. ................. 250/281
6,147,348 A * 11/2000 Quarmby et al. ............ 250/282
6,207,861 B1   3/2001 Nash et al. .................. 564/133

OTHER PUBLICATIONS

Zhongai Zhang and James S. Mcelvain, De Novo Peptide Sequencing by Two–Dimensional Fragment Correlation Mass Spectrometry, Analytical Chemistry, Jun. 1, 2000, pp. 2337–2350.

* cited by examiner

*Primary Examiner*—Hal Wachsman
(74) *Attorney, Agent, or Firm*—Fish & Richardson P.C.

(57) ABSTRACT

A method and apparatus are provided for identifying unknown chemical structures that are related to one or more known structures. Measured masses of the unknown structures (US members) are compared with the expected masses of the known structures (DS members). The mass differences between US members and DS members are compared with changes in mass ($\Delta M$) between molecules analyzed as a function dependent upon structure ($\Delta S$). The mass difference is considered as a differential function, $\Delta M/\Delta S$, the result of which is calculated for each ion in the US when compared with each ion in the DS. These values are then correlated with values that would be expected based on assumed possible structural modifications. In addition, higher order differential functions, such as $\Delta^2 M/\Delta S^2$, can be used as needed to allow for correlation of structures in which more than one structural motif has changed.

35 Claims, 23 Drawing Sheets

| Δ | Freq. | Δ | Freq. | Δ | Freq. | Δ | Freq. |
|---|---|---|---|---|---|---|---|
| 4 | 5 | 51 | 5 | 101 | 8 | 152 | 14 |
| 7 | 12 | 54 | 14 | 105 | 14 | 156 | 2 |
| 11 | 24 | 58 | 22 | 108 | 1 | 159 | 8 |
| 14 | 2 | 61 | 1 | 109 | 2 | 163 | 8 |
| 15 | 1 | 62 | 1 | 112 | 14 | 166 | 2 |
| 18 | 24 | 65 | 22 | 116 | 11 | 170 | 8 |
| 22 | 14 | 69 | 11 | 119 | 5 | 174 | 5 |
| 25 | 8 | 72 | 6 | 123 | 12 | 177 | 5 |
| 29 | 20 | 76 | 24 | 127 | 4 | 181 | 5 |
| 32 | 1 | 80 | 5 | 130 | 12 | 184 | 1 |
| 33 | 5 | 83 | 14 | 134 | 11 | 185 | 1 |
| 36 | 20 | 87 | 14 | 137 | 1 | 188 | 6 |
| 40 | 14 | 90 | 2 | 138 | 1 | 192 | 4 |
| 43 | 5 | 91 | 1 | 141 | 14 | 195 | 4 |
| 44 | 1 | 94 | 20 | 145 | 5 | 199 | 5 |
| 47 | 24 | 98 | 8 | 148 | 5 | | |

Delta mass frequency table for the desired set (shown up to mass 200)

SCHEMATIC PRIOR ART
DEPICTION OF STRUCTURAL
BUILDING BLOCKS

| BB | 42 | 115 | 123 | 307 |
|---|---|---|---|---|
| 42 | *99* | -47 | -11 | -65 |
| 115 | 47 | *146* | -58 | -18 |
| 123 | 11 | 58 | *88* | -76 |
| 307 | 65 | 18 | 76 | *164* |

Table 1: Building Block mass information for example library

Fig. 3

| | Mass | BBs contained | | | |
|---|---|---|---|---|---|
| 1 | 614 | 123 | 123 | 123 | 123 |
| 2 | 625 | 42 | 123 | 123 | 123 |
| 3 | 636 | 42 | 42 | 123 | 123 |
| 4 | 647 | 42 | 42 | 42 | 123 |
| 5 | 658 | 42 | 42 | 42 | 42 |
| 6 | 672 | 115 | 123 | 123 | 123 |
| 7 | 683 | 42 | 115 | 123 | 123 |
| 8 | 690 | 123 | 123 | 123 | 307 |
| 9 | 694 | 42 | 42 | 115 | 123 |
| 10 | 701 | 42 | 123 | 123 | 307 |
| 11 | 705 | 42 | 42 | 42 | 115 |
| 12 | 712 | 42 | 42 | 123 | 307 |
| 13 | 723 | 42 | 42 | 42 | 307 |
| 14 | 730 | 115 | 115 | 123 | 123 |
| 15 | 741 | 42 | 115 | 115 | 123 |
| 16 | 748 | 115 | 123 | 123 | 307 |
| 17 | 752 | 42 | 42 | 115 | 115 |
| 18 | 759 | 42 | 115 | 123 | 307 |
| 19 | 766 | 123 | 123 | 307 | 307 |
| 20 | 770 | 42 | 42 | 115 | 307 |
| 21 | 777 | 42 | 123 | 307 | 307 |
| 22 | 788 | 115 | 115 | 115 | 123 |
| 23 | 788 | 42 | 42 | 307 | 307 |
| 24 | 799 | 42 | 115 | 115 | 115 |
| 25 | 806 | 115 | 115 | 123 | 307 |
| 26 | 817 | 42 | 115 | 115 | 307 |
| 27 | 824 | 115 | 123 | 307 | 307 |
| 28 | 835 | 42 | 115 | 307 | 307 |
| 29 | 842 | 123 | 307 | 307 | 307 |
| 30 | 846 | 115 | 115 | 115 | 115 |
| 31 | 853 | 42 | 307 | 307 | 307 |
| 32 | 864 | 115 | 115 | 115 | 307 |
| 33 | 882 | 115 | 115 | 307 | 307 |
| 34 | 900 | 115 | 307 | 307 | 307 |
| 35 | 918 | 307 | 307 | 307 | 307 |

Table 2: BB Composition and masses for all 35 members of the desired set.

Table 3: partial listing of mass peaks measured that do not belong to the library

Fig. 5

|     | 606  | 612  | 742  | 640  | 956   | 994 |
|-----|------|------|------|------|-------|-----|
| 918 | -312 | -306 | -176 | -278 | 38    | 76  |
| 900 | -294 | -288 | -158 | -260 | 56    | 94  |
| 882 | -276 | -270 | -140 | -242 | 74    | 112 |
| 864 | -258 | -252 | -122 | -224 | 92    | 130 |
| 853 | -247 | -241 | -111 | -213 | 103   | 141 |
| 846 | -240 | -234 | -104 | -206 | 110   | 148 |
| 842 | -236 | -230 | -100 | -202 | 114   | 152 |
| 835 | -229 | -223 | -93  | -195 | 121   | 159 |
| 824 | -218 | -212 | -82  | -184 | 132   | 170 |
| 817 | -211 | -205 | -75  | -177 | 139   | 177 |
| 806 | -200 | -194 | -64  | -166 | 150   | 188 |
| 799 | -193 | -187 | -57  | -159 | 157   | 195 |
| 788 | -182 | -176 | -46  | -148 | 168   | 206 |
| 788 | -182 | -176 | -46  | -148 | 168   | 206 |
| 777 | -171 | -165 | -35  | -137 | 179   | 217 |
| 770 | -164 | -158 | -28  | -130 | 186   | 224 |
| 766 | -160 | -154 | -24  | -126 | 190   | 228 |
| 759 | -153 | -147 | -17  | -119 | 197   | 235 |
| 752 | -146 | -140 | -10  | -112 | 204   | 242 |
| 748 | -142 | -136 | -6   | -108 | 208   | 246 |
| 741 | -135 | -129 | 1    | -101 | 215   | 253 |
| 730 | -124 | -118 | 12   | -90  | 226   | 264 |
| 723 | -117 | -111 | 19   | -83  | 233   | 271 |
| 712 | -106 | -100 | 30   | -72  | 244   | 282 |
| 705 | -99  | -93  | 37   | -65  | 251   | 289 |
| 701 | -95  | -89  | 41   | -61  | 255   | 293 |
| 694 | -88  | -82  | 48   | -54  | 262   | 300 |
| 690 | -84  | -78  | 52   | -50  | 266   | 304 |
| 683 | -77  | -71  | 59   | -43  | 273   | 311 |
| 672 | -66  | -60  | 70   | -32  | 284   | 322 |
| 658 | -52  | -46  | 84   | -18  | 298   | 336 |
| 647 | -41  | -35  | 95   | -7   | 308-9 | 347 |
| 636 | -30  | -24  | 106  | 4    | 320   | 358 |
| 625 | -19  | -13  | 117  | 15   | 331   | 369 |
| 614 | -8   | -2   | 128  | 26   | 342   | 380 |

DMV table for the DS (vertical axis) versus the US (horizontal axis)

FIG. 6

| Mass | 1 Bu | 2 Bu | 3 Bu |
|---|---|---|---|
| 0 | 56 | 112 | 168 |

Mass displacement caused by butyl additions   FIG. 7

| BB | 42 | 115 | 123 | 307 | (-OH) |
|---|---|---|---|---|---|
| 42 | *99* | -47 | -11 | -65 | -82 |
| 115 | 47 | *146* | -58 | -18 | -129 |
| 123 | 11 | 58 | *88* | -76 | -71 |
| 307 | 65 | 18 | 76 | *164* | -147 |
| (-OH) | 82 | 129 | 71 | 147 | *17* |

Expansion of Fig. 3 to show the additional effects of hydroxyl group substration

FIG. 8

| -OH DMV | 1 Bu | 2 Bu | 3 Bu |
|---|---|---|---|
| -147 | -91 | -35 | 21 |
| -129 | -73 | -17 | 39 |
| -82 | -26 | 30 | 86 |
| -76 | -20 | 36 | 92 |
| -71 | -15 | 41 | 97 |
| -65 | -9 | 47 | 103 |
| -58 | -2 | 54 | 110 |
| -47 | 9 | 65 | 121 |
| -18 | 38 | 94 | 150 |
| -11 | 45 | 101 | 157 |

Net displacement of the hydroxyl DMVs from Fig. 8 resulting from butyl additions

FIG. 9

|     | 606  | 612  | 742  | 640  | 956   | 994 |
|-----|------|------|------|------|-------|-----|
| 918 | -312 | -306 | -176 | -278 | 38    | 76  |
| 900 | -294 | -288 | -158 | -260 | *56*  | 94  |
| 882 | -276 | -270 | -140 | -242 | 74    | *112* |
| 864 | -258 | -252 | -122 | -224 | 92    | 130 |
| 853 | -247 | -241 | -111 | -213 | 103   | 141 |
| 846 | -240 | -234 | -104 | -206 | 110   | 148 |
| 842 | -236 | -230 | -100 | -202 | 114   | 152 |
| 835 | -229 | -223 | -93  | -195 | 121   | 159 |
| 824 | -218 | -212 | -82  | -184 | 132   | 170 |
| 817 | -211 | -205 | -75  | -177 | 139   | 177 |
| 806 | -200 | -194 | -64  | -166 | 150   | 188 |
| 799 | -193 | -187 | -57  | -159 | 157   | 195 |
| 788 | -182 | -176 | -46  | -148 | *168* | 206 |
| 788 | -182 | -176 | -46  | -148 | *168* | 206 |
| 777 | -171 | -165 | -35  | -137 | 179   | 217 |
| 770 | -164 | -158 | -28  | -130 | 186   | 224 |
| 766 | -160 | -154 | -24  | -126 | 190   | 228 |
| 759 | -153 | -147 | -17  | -119 | 197   | 235 |
| 752 | -146 | -140 | -10  | -112 | 204   | 242 |
| 748 | -142 | -136 | -6   | -108 | 208   | 246 |
| 741 | -135 | -129 | 1    | -101 | 215   | 253 |
| 730 | -124 | -118 | 12   | -90  | 226   | 264 |
| 723 | -117 | -111 | 19   | -83  | 233   | 271 |
| 712 | -106 | -100 | 30   | -72  | 244   | 282 |
| 705 | -99  | -93  | 37   | -65  | 251   | 289 |
| 701 | -95  | -89  | 41   | -61  | 255   | 293 |
| 694 | -88  | -82  | 48   | -54  | 262   | 300 |
| 690 | -84  | -78  | 52   | -50  | 266   | 304 |
| 683 | -77  | -71  | 59   | -43  | 273   | 311 |
| 672 | -66  | -60  | 70   | -32  | 284   | 322 |
| 658 | -52  | -46  | 84   | -18  | 298   | 336 |
| 647 | -41  | -35  | 95   | -7   | 308-9 | 347 |
| 636 | -30  | -24  | 106  | 4    | 320   | 358 |
| 625 | -19  | -13  | 117  | 15   | 331   | 369 |
| 614 | -8   | -2   | 128  | 26   | 342   | 380 |

Table showing zero order addition co-incidences

FIG. 10

|     | 606  | 612  | 742  | 640  | 956   | 994 |
|-----|------|------|------|------|-------|-----|
| 918 | -312 | -306 | -176 | -278 | 38    | 76  |
| 900 | -294 | -288 | -158 | -260 | 56    | 94  |
| 882 | -276 | -270 | -140 | -242 | 74    | 112 |
| 864 | -258 | -252 | -122 | -224 | 92    | 130 |
| 853 | -247 | -241 | -111 | -213 | 103   | 141 |
| 846 | -240 | -234 | -104 | -206 | 110   | 148 |
| 842 | -236 | -230 | -100 | -202 | 114   | 152 |
| 835 | -229 | -223 | -93  | -195 | 121   | 159 |
| 824 | -218 | -212 | *-82* | -184 | 132  | 170 |
| 817 | -211 | -205 | -75  | -177 | 139   | 177 |
| 806 | -200 | -194 | -64  | -166 | 150   | 188 |
| 799 | -193 | -187 | -57  | -159 | 157   | 195 |
| 788 | -182 | -176 | -46  | -148 | 168   | 206 |
| 788 | -182 | -176 | -46  | -148 | 168   | 206 |
| 777 | -171 | -165 | -35  | -137 | 179   | 217 |
| 770 | -164 | -158 | -28  | -130 | 186   | 224 |
| 766 | -160 | -154 | -24  | -126 | 190   | 228 |
| 759 | -153 | *-147* | -17 | -119 | 197  | 235 |
| 752 | -146 | -140 | -10  | -112 | 204   | 242 |
| 748 | -142 | -136 | -6   | -108 | 208   | 246 |
| 741 | -135 | *-129* | 1  | -101 | 215   | 253 |
| 730 | -124 | -118 | 12   | -90  | 226   | 264 |
| 723 | -117 | -111 | 19   | -83  | 233   | 271 |
| 712 | -106 | -100 | 30   | -72  | 244   | 282 |
| 705 | -99  | -93  | 37   | *-65* | 251  | 289 |
| 701 | -95  | -89  | 41   | -61  | 255   | 293 |
| 694 | -88  | *-82* | 48  | -54  | 262   | 300 |
| 690 | -84  | -78  | 52   | -50  | 266   | 304 |
| 683 | -77  | *-71* | 59  | -43  | 273   | 311 |
| 672 | -66  | -60  | 70   | -32  | 284   | 322 |
| 658 | -52  | -46  | 84   | -18  | 298   | 336 |
| 647 | -41  | -35  | 95   | -7   | 308-9 | 347 |
| 636 | -30  | -24  | 106  | 4    | 320   | 358 |
| 625 | -19  | -13  | 117  | 15   | 331   | 369 |
| 614 | -8   | -2   | 128  | 26   | 342   | 380 |

Table showing first order substitution co-incidences

FIG. 11

|  | 606 | 612 | *742* | 640 | 956 | 994 |
|---|---|---|---|---|---|---|
| 918 | -312 | -306 | -176 | -278 | 38 | 76 |
| 900 | -294 | -288 | -158 | -260 | 56 | 94 |
| 882 | -276 | -270 | -140 | -242 | 74 | 112 |
| 864 | -258 | -252 | -122 | -224 | 92 | 130 |
| 853 | -247 | -241 | -111 | -213 | 103 | 141 |
| 846 | -240 | -234 | -104 | -206 | 110 | 148 |
| 842 | -236 | -230 | -100 | -202 | 114 | 152 |
| 835 | -229 | -223 | -93 | -195 | 121 | 159 |
| 824 | -218 | -212 | -82 | -184 | 132 | 170 |
| 817 | -211 | -205 | -75 | -177 | 139 | 177 |
| 806 | -200 | -194 | -64 | -166 | 150 | 188 |
| 799 | -193 | -187 | -57 | -159 | 157 | 195 |
| 788 | -182 | -176 | -46 | -148 | 168 | 206 |
| 788 | -182 | -176 | -46 | -148 | 168 | 206 |
| 777 | -171 | -165 | *-35* | -137 | 179 | 217 |
| 770 | -164 | -158 | -28 | -130 | 186 | 224 |
| 766 | -160 | -154 | -24 | -126 | 190 | 228 |
| 759 | -153 | -147 | *-17* | -119 | 197 | 235 |
| 752 | -146 | -140 | -10 | -112 | 204 | 242 |
| 748 | -142 | -136 | -6 | -108 | 208 | 246 |
| 741 | -135 | -129 | 1 | -101 | 215 | 253 |
| 730 | -124 | -118 | 12 | -90 | 226 | 264 |
| 723 | -117 | -111 | 19 | -83 | 233 | 271 |
| 712 | -106 | -100 | *30* | -72 | 244 | 282 |
| 705 | -99 | -93 | 37 | -65 | 251 | 289 |
| 701 | -95 | -89 | *41* | -61 | 255 | 293 |
| 694 | -88 | -82 | 48 | -54 | 262 | 300 |
| 690 | -84 | -78 | 52 | -50 | 266 | 304 |
| 683 | -77 | -71 | 59 | -43 | 273 | 311 |
| 672 | -66 | -60 | 70 | -32 | 284 | 322 |
| 658 | -52 | -46 | 84 | -18 | 298 | 336 |
| 647 | -41 | *-35* | 95 | -7 | 309 | 347 |
| 636 | -30 | -24 | 106 | 4 | 320 | 358 |
| 625 | -19 | -13 | 117 | 15 | 331 | 369 |
| 614 | -8 | -2 | 128 | 26 | 342 | 380 |

Table showing effect of first order substitutions plus additions

FIG. 12

| dM/dS | -71 | -82 | -129 | -147 |
|---|---|---|---|---|
| -71 | -142 | -153 | -200 | -218 |
| -82 | -153 | -164 | -211 | -229 |
| -129 | -200 | -211 | -258 | -276 |
| -147 | -218 | -229 | -276 | -294 |

Second order delta mass values (Hydroxyl substitutions only)

FIG. 13

| DMV | 1 Bu | 2 Bu | 3 Bu |
|---|---|---|---|
| -294 | -238 | -182 | -126 |
| -276 | -220 | -164 | -108 |
| -258 | -202 | -146 | -90 |
| -229 | -173 | -117 | -61 |
| -218 | -162 | -106 | -50 |
| -211 | -155 | -99 | -43 |
| -200 | -144 | -88 | -32 |
| -164 | -108 | -52 | 4 |
| -153 | -97 | -41 | 15 |
| -142 | -86 | -30 | 26 |

Butyl addition displacement of Fig. 13

FIG. 14

|  | 606 | 612 | 742 | 640 | 956 | 994 |
|---|---|---|---|---|---|---|
| 918 | -312 | -306 | -176 | -278 | 38 | 76 |
| 900 | *-294* | -288 | -158 | -260 | 56 | 94 |
| 882 | *-276* | -270 | -140 | -242 | 74 | 112 |
| 864 | *-258* | -252 | -122 | -224 | 92 | 130 |
| 853 | -247 | -241 | -111 | -213 | 103 | 141 |
| 846 | -240 | -234 | -104 | -206 | 110 | 148 |
| 842 | -236 | -230 | -100 | -202 | 114 | 152 |
| 835 | *-229* | -223 | -93 | -195 | 121 | 159 |
| 824 | *-218* | -212 | -82 | -184 | 132 | 170 |
| 817 | *-211* | -205 | -75 | -177 | 139 | 177 |
| 806 | *-200* | -194 | -64 | -166 | 150 | 188 |
| 799 | -193 | -187 | -57 | -159 | 157 | 195 |
| 788 | -182 | -176 | -46 | -148 | 168 | 206 |
| 788 | -182 | -176 | -46 | -148 | 168 | 206 |
| 777 | -171 | -165 | -35 | -137 | 179 | 217 |
| 770 | *-164* | -158 | -28 | -130 | 186 | 224 |
| 766 | -160 | -154 | -24 | -126 | 190 | 228 |
| 759 | *-153* | -147 | -17 | -119 | 197 | 235 |
| 752 | -146 | -140 | -10 | -112 | 204 | 242 |
| 748 | *-142* | -136 | -6 | -108 | 208 | 246 |
| 741 | -135 | -129 | 1 | -101 | 215 | 253 |
| 730 | -124 | -118 | 12 | -90 | 226 | 264 |
| 723 | -117 | -111 | 19 | -83 | 233 | 271 |
| 712 | -106 | -100 | 30 | -72 | 244 | 282 |
| 705 | -99 | -93 | 37 | -65 | 251 | 289 |
| 701 | -95 | -89 | 41 | -61 | 255 | 293 |
| 694 | -88 | -82 | 48 | -54 | 262 | 300 |
| 690 | -84 | -78 | 52 | -50 | 266 | 304 |
| 683 | -77 | -71 | 59 | -43 | 273 | 311 |
| 672 | -66 | -60 | 70 | -32 | 284 | 322 |
| 658 | -52 | -46 | 84 | -18 | 298 | 336 |
| 647 | -41 | *-35* | 95 | -7 | 309 | 347 |
| 636 | -30 | -24 | 106 | 4 | 320 | 358 |
| 625 | -19 | -13 | 117 | 15 | 331 | 369 |
| 614 | -8 | -2 | 128 | 26 | 342 | 380 |

Table showing effect of second order substitutions

FIG. 15

|     | 606  | 612  | 742  | *640* | 956 | 994 |
|-----|------|------|------|-------|-----|-----|
| 918 | -312 | -306 | -176 | -278  | 38  | 76  |
| 900 | -294 | -288 | -158 | -260  | 56  | 94  |
| 882 | -276 | -270 | -140 | -242  | 74  | 112 |
| 864 | -258 | -252 | -122 | -224  | 92  | 130 |
| 853 | -247 | -241 | -111 | -213  | 103 | 141 |
| 846 | -240 | -234 | -104 | -206  | 110 | 148 |
| 842 | -236 | -230 | -100 | -202  | 114 | 152 |
| 835 | -229 | -223 | -93  | -195  | 121 | 159 |
| 824 | -218 | -212 | -82  | -184  | 132 | 170 |
| 817 | -211 | -205 | -75  | -177  | 139 | 177 |
| 806 | -200 | -194 | -64  | -166  | 150 | 188 |
| 799 | -193 | -187 | -57  | -159  | 157 | 195 |
| 788 | -182 | -176 | -46  | -148  | 168 | 206 |
| 788 | -182 | -176 | -46  | -148  | 168 | 206 |
| 777 | -171 | -165 | -35  | -137  | 179 | 217 |
| 770 | -164 | -158 | -28  | -130  | 186 | 224 |
| 766 | -160 | -154 | -24  | *-126*| 190 | 228 |
| 759 | -153 | -147 | -17  | -119  | 197 | 235 |
| 752 | -146 | -140 | -10  | -112  | 204 | 242 |
| 748 | -142 | -136 | -6   | *-108*| 208 | 246 |
| 741 | -135 | -129 | 1    | -101  | 215 | 253 |
| 730 | -124 | -118 | 12   | *-90* | 226 | 264 |
| 723 | -117 | -111 | 19   | -83   | 233 | 271 |
| 712 | -106 | -100 | 30   | -72   | 244 | 282 |
| 705 | -99  | -93  | 37   | -65   | 251 | 289 |
| 701 | -95  | -89  | 41   | *-61* | 255 | 293 |
| 694 | -88  | -82  | 48   | -54   | 262 | 300 |
| 690 | -84  | -78  | 52   | *-50* | 266 | 304 |
| 683 | -77  | -71  | 59   | *-43* | 273 | 311 |
| 672 | -66  | -60  | 70   | *-32* | 284 | 322 |
| 658 | -52  | -46  | 84   | -18   | 298 | 336 |
| 647 | -41  | -35  | 95   | -7    | 309 | 347 |
| 636 | -30  | -24  | 106  | *4*   | 320 | 358 |
| 625 | -19  | -13  | 117  | *15*  | 331 | 369 |
| 614 | -8   | -2   | 128  | *26*  | 342 | 380 |

Table showing effect of second order substitutions plus additions

FIG. 16

| Undesired set mass | Substitutions | | | | Additions |
|---|---|---|---|---|---|
| 606 | hydroxyl | hydroxyl | 115 | 307 | |
| 612 | hydroxyl | 42 | 115 | 123 | |
| 640 | hydroxyl | hydroxyl | 123 | 123 | 3 butyls |
| 742 | hydroxyl | 42 | 123 | 307 | 2 butyls |
| 956 | 115 | 307 | 307 | 307 | 1 butyl |
| | 115 | 115 | 115 | 123 | 3 butyls |
| | 42 | 42 | 307 | 307 | 3 butyls |
| 994 | 115 | 115 | 307 | 307 | 2 butyls |

Summary of possible structures for some members of the undesired set.

FIG. 17

| Δ | Freq. | Δ | Freq. | Δ | Freq. | Δ | Freq. |
|---|---|---|---|---|---|---|---|
| 4 | 5 | 51 | 5 | 101 | 8 | 152 | 14 |
| 7 | 12 | 54 | 14 | 105 | 14 | 156 | 2 |
| 11 | 24 | 58 | 22 | 108 | 1 | 159 | 8 |
| 14 | 2 | 61 | 1 | 109 | 2 | 163 | 8 |
| 15 | 1 | 62 | 1 | 112 | 14 | 166 | 2 |
| 18 | 24 | 65 | 22 | 116 | 11 | 170 | 8 |
| 22 | 14 | 69 | 11 | 119 | 5 | 174 | 5 |
| 25 | 8 | 72 | 6 | 123 | 12 | 177 | 5 |
| 29 | 20 | 76 | 24 | 127 | 4 | 181 | 5 |
| 32 | 1 | 80 | 5 | 130 | 12 | 184 | 1 |
| 33 | 5 | 83 | 14 | 134 | 11 | 185 | 1 |
| 36 | 20 | 87 | 14 | 137 | 1 | 188 | 6 |
| 40 | 14 | 90 | 2 | 138 | 1 | 192 | 4 |
| 43 | 5 | 91 | 1 | 141 | 14 | 195 | 4 |
| 44 | 1 | 94 | 20 | 145 | 5 | 199 | 5 |
| 47 | 24 | 98 | 8 | 148 | 5 | | |

Delta mass frequency table for the desired set (shown up to mass 200)

Partial list of members of the undesired set

FIG. 19

| Δ | Freq. | Δ | Freq. | Δ | Freq. | Δ | Freq. |
|---|---|---|---|---|---|---|---|
| 2 | 2 | 54 | 1 | 100 | 1 | 150 | 2 |
| 7 | 2 | 56 | 6 | 101 | 1 | 156 | 1 |
| 9 | 3 | 58 | 2 | 103 | 1 | 157 | 1 |
| 11 | 3 | 62 | 1 | 110 | 1 | 159 | 1 |
| 18 | 9 | 63 | 1 | 112 | 4 | 166 | 1 |
| 19 | 1 | 65 | 3 | 114 | 1 | 168 | 2 |
| 20 | 4 | 74 | 4 | 118 | 1 | 170 | 1 |
| 22 | 1 | 76 | 2 | 119 | 1 | 174 | 1 |
| 25 | 1 | 81 | 1 | 121 | 2 | 175 | 1 |
| 27 | 2 | 83 | 2 | 130 | 3 | 177 | 2 |
| 29 | 3 | 92 | 2 | 132 | 2 | 186 | 1 |
| 36 | 3 | 94 | 3 | 137 | 1 | 188 | 2 |
| 38 | 5 | | | 139 | 2 | 192 | 1 |
| 40 | 2 | | | 148 | 2 | 193 | 1 |
| 44 | 1 | | | | | 195 | 2 |
| 45 | 1 | | | | | | |
| 47 | 3 | | | | | | |

Delta Mass frequency table for the undesired set

FIG. 20

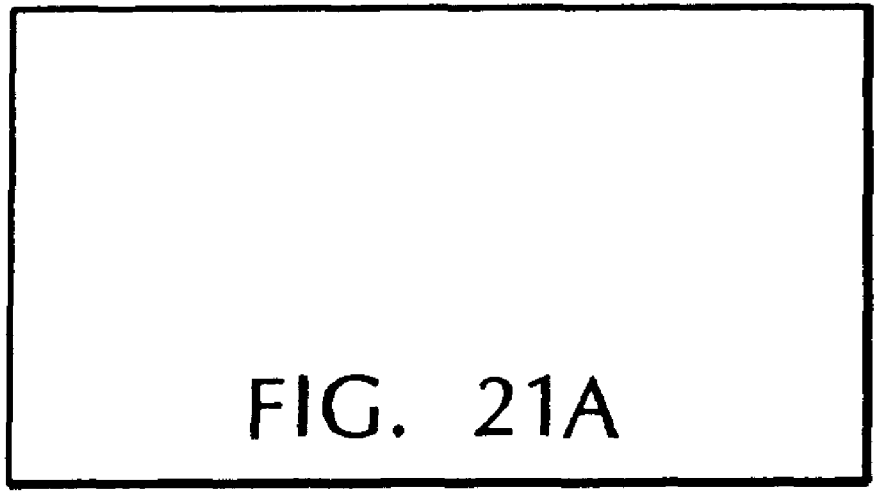
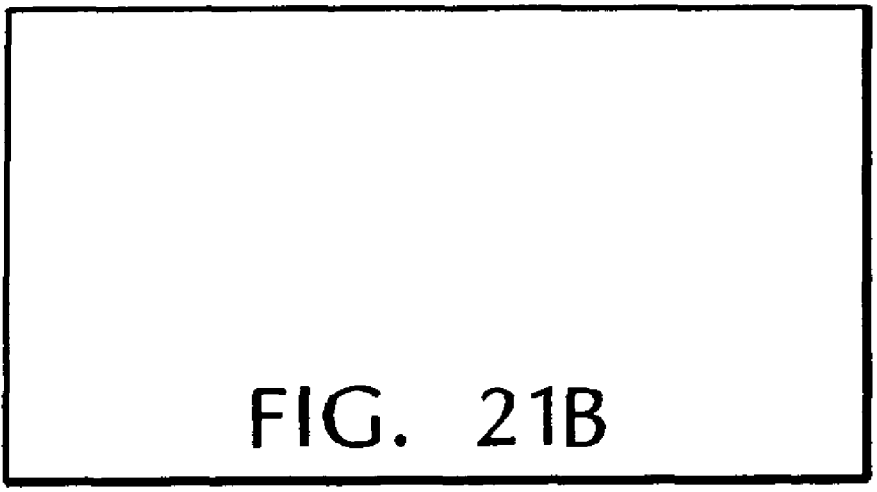
FIG. 21

| UNDESIRED SET | | | DESIRED SET | |
|---|---|---|---|---|
| Rank | DMV | Frequency | Rank | DMV | Frequency |
| 1 | 18 | 9 | 1 | 11 | 24 |
| 2 | 56 | 6 | 1 | 18 | 24 |
| 3 | 38 | 5 | 1 | 47 | 24 |
| 4 | 20 | 4 | 1 | 76 | 24 |
| 4 | 74 | 4 | 2 | 58 | 22 |
| 4 | 112 | 4 | 2 | 65 | 22 |
| 5 | 9 | 3 | 3 | 29 | 20 |
| 5 | 11 | 3 | 3 | 36 | 20 |
| 5 | 29 | 3 | 3 | 94 | 20 |
| 5 | 36 | 3 | 4 | 22 | 14 |
| 5 | 47 | 3 | 4 | 40 | 14 |
| 5 | 65 | 3 | 4 | 54 | 14 |
| 5 | 94 | 3 | 4 | 83 | 14 |
| 5 | 130 | 3 | 4 | 87 | 14 |
| 6 | 2 | 2 | 4 | 105 | 14 |
| 6 | 7 | 2 | 4 | 112 | 14 |
| 6 | 27 | 2 | 4 | 141 | 14 |
| 6 | 40 | 2 | 4 | 152 | 14 |
| 6 | 58 | 2 | 5 | 7 | 12 |
| 6 | 76 | 2 | 5 | 123 | 12 |
| 6 | 83 | 2 | 5 | 130 | 12 |
| 6 | 92 | 2 | 6 | 69 | 11 |
| 6 | 121 | 2 | 6 | 116 | 11 |
| 6 | 132 | 2 | 6 | 134 | 11 |
| 6 | 139 | 2 | 7 | 25 | 8 |
| 6 | 148 | 2 | 7 | 98 | 8 |
| 6 | 150 | 2 | 7 | 101 | 8 |
| 6 | 168 | 2 | 7 | 159 | 8 |
| 6 | 177 | 2 | 7 | 163 | 8 |

FIG. 21A

DMF tables for the Undesired Set (left) and the Desired Set (right), ranked by frequency

| UNDESIRED SET | | | DESIRED SET | |
|---|---|---|---|---|
| 6 | 188 | 2 | 170 | 8 |
| 6 | 195 | 2 | 72 | 6 |
| 7 | 19 | 1 | 188 | 6 |
| 7 | 22 | 1 | 4 | 5 |
| 7 | 25 | 1 | 33 | 5 |
| 7 | 44 | 1 | 43 | 5 |
| 7 | 45 | 1 | 51 | 5 |
| 7 | 54 | 1 | 80 | 5 |
| 7 | 62 | 1 | 119 | 5 |
| 7 | 63 | 1 | 145 | 5 |
| 7 | 81 | 1 | 148 | 5 |
| 7 | 100 | 1 | 174 | 5 |
| 7 | 101 | 1 | 177 | 5 |
| 7 | 103 | 1 | 181 | 5 |
| 7 | 110 | 1 | 199 | 5 |
| 7 | 114 | 1 | 127 | 4 |
| 7 | 118 | 1 | 192 | 4 |
| 7 | 119 | 1 | 195 | 4 |
| 7 | 137 | 1 | 14 | 2 |
| 7 | 156 | 1 | 90 | 2 |
| 7 | 157 | 1 | 109 | 2 |
| 7 | 159 | 1 | 156 | 2 |
| 7 | 166 | 1 | 166 | 2 |
| 7 | 170 | 1 | 15 | 1 |
| 7 | 174 | 1 | 32 | 1 |
| 7 | 175 | 1 | 44 | 1 |
| 7 | 186 | 1 | 61 | 1 |
| 7 | 192 | 1 | 62 | 1 |
| 7 | 193 | 1 | 91 | 1 |
| | | | 108 | 1 |
| | | | 137 | 1 |
| | | | 138 | 1 |
| | | | 184 | 1 |
| | | | 185 | 1 |

FIG. 21B  DMF tables for the Undesired Set (left) and the Desired Set (right), ranked by frequency

| Undesired Set | | | | Desired Set | | | | |
|---|---|---|---|---|---|---|---|---|
| Rank | DMV | Frequency | Rank | DMV | Frequency | US Rank | DS Rank | Score | Score + Bu |
| 1 | 18 | 9 | 1 | 11 | 24 | 1 | 1 | 2 | 2 |
| 2 | 56 | 6 | 1 | 18 | 24 | 2 | - | 10 bu | 2 |
| 3 | 38 | 5 | 1 | 47 | 24 | 3 | - | 10 56-18 | 4 |
| 4 | 20 | 4 | 1 | 76 | 24 | 4 | - | 10 56-36 | 7 |
| 4 | 74 | 4 | 2 | 58 | 22 | 4 | - | 10 56+18 | 5 |
| 4 | 112 | 4 | 2 | 65 | 22 | 4 | - | 10 2 bu | 2 |
| 5 | 9 | 3 | 3 | 29 | 20 | 5 | - | 10 56-47 | 6 |
| 5 | 11 | 3 | 3 | 36 | 20 | 5 | 1 | 6 | 6 |
| 5 | 29 | 3 | 3 | 94 | 20 | 5 | 3 | 8 | 8 |
| 5 | 36 | 3 | 4 | 22 | 14 | 5 | 3 | 8 | 8 |
| 5 | 47 | 3 | 4 | 40 | 14 | 5 | 1 | 6 | 6 |
| 5 | 65 | 3 | 4 | 54 | 14 | 5 | 2 | 7 | 7 |
| 5 | 94 | 3 | 4 | 83 | 14 | 5 | 3 | 8 | 8 |
| 5 | 130 | 3 | 4 | 87 | 14 | 5 | 5 | 10 | 10 |
| 6 | 2 | 2 | 4 | 105 | 14 | | | | |
| 6 | 7 | 2 | 4 | 112 | 14 | | | | |
| 6 | 27 | 2 | 4 | 141 | 14 | | | | |
| 6 | 40 | 2 | 4 | 152 | 14 | | | | |
| | | | | | | n = 14 Sum | | 115 | 81 |
| | | | | | | | Score = | 1.785714 | 4.214286 |

Example of simple scoring system for DMF analysis. Score = 10 −(Sum of rank in US + Sum or rank in DS); No presence = 10; Higher net final score implies higher correlation

FIG. 22

| Amino Acid | Mass | G 57 | A 71 | S 87 | P 97 | V 99 | T 101 | C 103 | I 113 | L 113 | N 114 | D 115 | Q 128 | K 128 | E 129 | M 131 | H 137 | F 147 | R 156 | Y 163 | W 186 |
|---|---|---|---|---|---|---|---|---|---|---|---|---|---|---|---|---|---|---|---|---|---|
| Glycine | 57 | 0 | 14 | 30 | 40 | 42 | 44 | 46 | 56 | 56 | 57 | 58 | 71 | 71 | 72 | 74 | 80 | 90 | 88 | 106 | 129 |
| Alanine | 71 | -14 | 0 | 16 | 26 | 28 | 30 | 32 | 42 | 42 | 43 | 44 | 57 | 57 | 58 | 60 | 66 | 76 | 85 | 92 | 115 |
| Serine | 87 | -30 | -16 | 0 | 10 | 12 | 14 | 16 | 26 | 26 | 27 | 28 | 41 | 41 | 42 | 44 | 50 | 60 | 69 | 76 | 99 |
| Proline | 97 | -40 | -26 | -10 | 0 | 2 | 4 | 6 | 16 | 16 | 17 | 18 | 31 | 31 | 32 | 34 | 40 | 50 | 59 | 66 | 89 |
| Valine | 99 | -42 | -28 | -12 | -2 | 0 | 2 | 4 | 14 | 14 | 15 | 16 | 29 | 29 | 30 | 32 | 38 | 48 | 57 | 64 | 87 |
| Threonine | 101 | -44 | -30 | -14 | -4 | -2 | 0 | 2 | 12 | 12 | 13 | 14 | 27 | 27 | 28 | 30 | 36 | 46 | 55 | 62 | 85 |
| Cysteine | 103 | -46 | -32 | -16 | -6 | -4 | -2 | 0 | 10 | 10 | 11 | 12 | 25 | 25 | 26 | 28 | 34 | 44 | 53 | 60 | 83 |
| Isoleucine | 113 | -56 | -42 | -26 | -16 | -14 | -12 | -10 | 0 | 0 | 1 | 2 | 15 | 15 | 16 | 18 | 24 | 34 | 43 | 50 | 73 |
| Leucine | 113 | -56 | -42 | -26 | -16 | -14 | -12 | -10 | 0 | 0 | 1 | 2 | 15 | 15 | 16 | 18 | 24 | 34 | 43 | 50 | 73 |
| Asparagine | 114 | -57 | -43 | -27 | -17 | -15 | -13 | -11 | -1 | -1 | 0 | 1 | 14 | 14 | 15 | 17 | 23 | 33 | 42 | 49 | 72 |
| Aspartic Acid | 115 | -58 | -44 | -28 | -18 | -16 | -14 | -12 | -2 | -2 | -1 | 0 | 13 | 13 | 14 | 16 | 22 | 32 | 41 | 48 | 71 |
| Glutamine | 128 | -71 | -57 | -41 | -31 | -29 | -27 | -25 | -15 | -15 | -14 | -13 | 0 | 0 | 1 | 3 | 9 | 19 | 28 | 35 | 58 |
| Lysine | 128 | -71 | -57 | -41 | -31 | -29 | -27 | -25 | -15 | -15 | -14 | -13 | 0 | 0 | 1 | 3 | 9 | 19 | 28 | 35 | 58 |
| Glutamic Acid | 129 | -72 | -58 | -42 | -32 | -30 | -28 | -26 | -16 | -16 | -15 | -14 | -1 | -1 | 0 | 2 | 8 | 18 | 27 | 34 | 57 |
| Methionine | 131 | -74 | -60 | -44 | -34 | -32 | -30 | -28 | -18 | -18 | -17 | -16 | -3 | -3 | -2 | 0 | 6 | 16 | 25 | 32 | 55 |
| Histidine | 137 | -80 | -66 | -50 | -40 | -38 | -36 | -34 | -24 | -24 | -23 | -22 | -9 | -9 | -8 | -6 | 0 | 10 | 19 | 26 | 49 |
| Phenylalanine | 147 | -90 | -76 | -60 | -50 | -48 | -46 | -44 | -34 | -34 | -33 | -32 | -19 | -19 | -18 | -16 | -10 | 0 | 9 | 16 | 39 |
| Arginine | 156 | -99 | -85 | -69 | -59 | -57 | -55 | -53 | -43 | -43 | -42 | -41 | -28 | -28 | -27 | -25 | -19 | -9 | 0 | 7 | 30 |
| Tyrosine | 163 | -106 | -92 | -76 | -66 | -64 | -62 | -60 | -50 | -50 | -49 | -48 | -35 | -35 | -34 | -32 | -26 | -16 | -7 | 0 | 23 |
| Tryptophan | 186 | -129 | -115 | -99 | -89 | -87 | -85 | -83 | -73 | -73 | -72 | -71 | -58 | -58 | -57 | -55 | -49 | -39 | -30 | -23 | 0 |

Delta Mass Value Table for the 20 naturally occurring amino acids

FIG. 23

|     | 480 | 409 | 363 | 351 | 335 | 329 | 301 | 285 | 275 | 247 | 232 | 229 | 218 | 204 | 135 | 118 | 107 | 84 |
|-----|-----|-----|-----|-----|-----|-----|-----|-----|-----|-----|-----|-----|-----|-----|-----|-----|-----|----|
| 480 | 0   |     |     |     |     |     |     |     |     |     |     |     |     |     |     |     |     |    |
| 409 | 71  | 0   |     |     |     |     |     |     |     |     |     |     |     |     |     |     |     |    |
| 363 | 117 | *46* | 0  |     |     |     |     |     |     |     |     |     |     |     |     |     |     |    |
| 351 | 129 | 58  | 12  | 0   |     |     |     |     |     |     |     |     |     |     |     |     |     |    |
| 335 | 145 | 74  | *28* | 16 | 0   |     |     |     |     |     |     |     |     |     |     |     |     |    |
| 329 | *151* | 80 | 34 | 22 | 6 | 0 |     |     |     |     |     |     |     |     |     |     |     |    |
| 301 | 179 | 108 | 62 | 50 | 34 | *28* | 0 |     |     |     |     |     |     |     |     |     |     |    |
| 285 | 195 | 124 | 78 | 66 | 50 | 44 | 16 | 0 |     |     |     |     |     |     |     |     |     |    |
| 275 | 205 | *134* | 88 | 76 | 60 | 54 | 26 | 10 | 0 |     |     |     |     |     |     |     |     |    |
| 247 | 233 | 162 | 116 | 104 | 88 | 82 | 54 | 38 | *28* | 0 |     |     |     |     |     |     |     |    |
| 232 | 248 | 177 | 131 | 119 | 103 | 97 | 69 | 53 | 43 | 15 | 0 |     |     |     |     |     |     |    |
| 229 | 251 | 180 | *134* | 122 | 106 | 100 | 72 | 56 | *46* | *18* | 3 | 0 |     |     |     |     |     |    |
| 218 | 262 | 191 | 145 | 133 | 117 | 111 | 83 | 67 | 57 | 29 | 14 | 11 | 0 |     |     |     |     |    |
| 204 | 276 | 205 | 159 | 147 | 131 | 125 | 97 | 81 | 71 | 43 | *28* | 25 | 14 | 0 |     |     |     |    |
| 135 | 345 | 274 | 228 | 216 | 200 | 194 | 166 | 150 | 140 | 112 | 97 | 94 | 83 | 69 | 0 |     |     |    |
| 118 | 362 | 291 | 245 | 233 | 217 | 211 | 183 | 167 | 157 | 129 | 114 | 111 | 100 | 86 | 17 | 0 |     |    |
| 107 | 373 | 302 | 256 | 244 | 228 | 222 | 194 | 178 | 168 | 140 | 125 | 122 | 111 | 97 | *28* | 11 | 0 |    |
| 84  | 396 | 325 | 279 | 267 | 251 | 245 | 217 | 201 | 191 | 163 | 148 | 145 | *134* | 120 | 51 | 24 | 23 | 0 |

DMV table for the MSMS spectrum shown in Figure 25. Structurally important DMVs are shown in *italics*.

FIG. 24

MS/MS mass spectrum, the significant masses of which are represented in the mass table of FIG. 24

METHOD AND APPARATUS FOR IDENTIFYING UNKNOWN COMPOUNDS IN COMPLEX CHEMICAL MIXTURES USING MASS SPECTROMETRY AND MASS DIFFERENTIAL ANALYSIS

FIELD OF THE INVENTION

The present invention relates generally to identifying unknown compounds in chemical mixtures and, more particularly, to identifying unknown chemical structures related to one or more known structures.

BACKGROUND OF THE INVENTION

Mass Spectrometry

Mass spectrometry (MS) is an analytical technique used to investigate molecular structure. It functions by first ionizing a sample under investigation, and then measuring the ion's mass-to-charge (m/z) ratio. In this way, the molecular weight of a substance may be determined, which is generally an important piece of information because all molecules of the same structure have the same molecular weight. This determination can thereby be considered as a "fingerprint" for a given structure.

MS is useful in analyzing complex mixtures because it can be used to obtain a molecular weight for each component of the mixture. This approach can be used when seeking to identify the presence or absence of a known material in the presence of many other materials. Common examples are the identification of drugs of abuse in blood and urine, and the identification of dioxins and other priority pollutants in soil samples.

If a complex mixture is admitted into a mass spectrometer all together, the resulting mass spectrum is an aggregate spectrum of all the species present. This makes it difficult to identify individual species. To solve this problem, complex mixtures analysis is usually performed by interfacing some form of chromatographic separation technique with the mass spectrometer. The purpose of this is to provide some level of separation for the mixture prior to the components entering the mass spectrometer. In ideal circumstances, it is then possible to obtain a mass spectrum of each individual component as it enters the mass spectrometer. In these cases, the retention time of each component on the chromatograph affords an additional level of identification.

Use of Mass Spectrometry in Drug Discovery

Drug discovery involves identifying new molecules that have potential use as drugs and other therapeutic agents. The new molecules can be discovered by examining the interaction of target proteins in solution with mixtures of organic molecules. The mixtures are known as 'libraries' of molecules, from which new species of interest can be identified. The libraries can be designed and synthesized according to a variety of rules and constraints that make them suitable for drug discovery. Molecules that bind to a target protein are known as ligands. Ligands have the potential to act as therapeutic agents.

Ligands can be discovered using mass spectrometry. One criterion of library design is that the masses of the component library members are calculated and known beforehand. When a ligand is discovered, its mass serves to identify the component and therefore the molecular structure responsible for binding.

Construction of Chemical Libraries

Libraries comprise mixtures of molecules made up of a core structure coupled with a selected number of different structural motifs known as 'building blocks' (BBs). FIG. 1 is a simplified schematic diagram illustrating a core structure 10 and three BBs 12, 14, 16 coupled to the core.

The number of BBs coupled to a given structural core is usually in the range from two to four, though many more such as, e.g., 15 different BBs may be coupled in any given library. A library should contain every combination and permutation of BBs possible. Also, the chemistry is performed such that the library is intended to contain only molecules that are members of the library, and no other significant molecular species. In other words, a library is intended to be a set of desired compounds, which is designated hereafter as the "desired set" (DS), whose individual compositions and masses may be calculated beforehand.

In practice, however, empirical measurements show that the chemistry involved in the synthesis of libraries does not always proceed in an expected fashion. Sometimes, certain members of the DS are not generated. Furthermore, in addition to the DS, many libraries contain molecular species that are not intended members of the library, designated hereafter as the "undesired set" (US). An US can arise as a result of unexpected deviations in the behavior of the synthetic chemistry. Since these deviations might not be anticipated, the size and composition of this set is unpredictable. However, since all of the reagents used in the synthesis were originally designed to become library members, most, if not all, members of the US will be structurally related to some member or members of the DS.

The presence of the US has two consequences of particular importance at the practical level. First, presence of the US has the effect of reducing the number of molecules belonging to the DS. Without knowing the magnitude of this effect, it is impossible to control the quantity of library exposed to the target for screening purposes. Therefore one advantage of identifying members of the US is that it allows a measure of synthesis quality control that cannot be otherwise obtained. A further advantage is that the output it provides can be used to assign a score, or rating, to library quality and thereby automatically eliminate its use in the screening process when the library quality is deemed too low.

Second, members of the US can sometimes themselves bind to the target protein. This manifests itself as follows. Binding is observed between the target and a sample member whose mass corresponds to that of a library member (a member of the DS). However, further structural analysis reveals that the ligand in fact has a structure that does not correspond to any member of the DS having the ligand's mass. Thus, the experiment has revealed a binding molecule, which was the desired objective of the experiment, but that binding molecule does not have a structure consistent with any member of the DS. A need now exists to identify the structure of the binding molecule to allow an analyst to gain insights into possible structures of ligands that are not members of the DS, but whose structures are related to those of the DS.

SUMMARY OF THE INVENTION

Briefly, the present invention is directed to a method and apparatus for identifying unknown chemical structures that are related to one or more known structures. In accordance with the invention, measured masses of the unknown structures (US members) are compared with the expected masses of the known structures (DS members). The mass differences between US members and DS members are compared with changes in mass ($\Delta M$) between molecules analyzed as a function dependent upon structure ($\Delta S$). The mass difference is considered as a differential function, $\Delta M/\Delta S$, the result of which is calculated for each ion in the US when compared with each ion in the DS. These values are then correlated with values that would be expected based on assumed possible structural modifications. In addition, higher order differential functions, such as $\Delta^2 M/\Delta S^2$, can be used as needed to allow for correlation of structures in which more than one structural motif has changed.

These and other features of the present invention will become readily apparent from the following detailed description wherein embodiments of the invention are shown and described by way of illustration of the best mode of the invention. As will be realized, the invention is capable of other and different embodiments and its several details may be capable of modifications in various respects, all without departing from the invention. Accordingly, the drawings and description are to be regarded as illustrative in nature and not in a restrictive or limiting sense with the scope of the application being indicated in the claims.

BRIEF DESCRIPTION OF THE DRAWINGS

For a fuller understanding of the nature and objects of the present invention, reference should be made to the following detailed description taken in connection with the accompanying drawings wherein:

FIG. 3 is a table listing building block delta mass values of an example library.

FIG. 4 is a table listing building block composition and masses for members of a desired set of the example library.

FIG. 5 is a table listing mass peaks belonging to an undesired set not belonging to the example library.

FIG. 6 is a table listing delta mass values for the desired and undesired sets in the examples.

FIG. 7 is a table listing mass displacement caused by butyl additions in the example.

FIG. 8 is a table listing the expansion of FIG. 3 to show the additional effects of a hydroxyl group substitution in the example.

FIG. 9 is a table listing the displacement of FIG. 8 values caused by butyl additions.

FIG. 10 is a table showing zero order addition coincidences in the example.

FIG. 11 is a table showing first order substitution coincidences in the example.

FIG. 12 is a table showing the effect of first order substitutions plus additions in the example.

FIG. 13 is a table showing second order delta mass values in the example.

FIG. 14 is a table showing the butyl addition displacement of FIG. 13 values in the example.

FIG. 15 is a table showing the effect of second order substitutions in the example.

FIG. 16 is a table showing the effect of second order substitutions plus additions in the example.

FIG. 17 is a table showing a summary of possible structures for some members of the undesired set in the example.

FIG. 18 is a table showing delta mass frequency values for the desired set in the example.

FIG. 19 is a table listing members of an undesired set in the example.

FIG. 20 is a table showing delta mass frequency values for the undesired set in the example.

FIG. 21 is a table showing delta mass frequency values for an undesired set and a desired set ranked by frequency in the example, as delineated in FIGS. 21A and 21B. FIGS. 21A and 21B are a table showing delta mass frequency values for an undesired set and a desired set ranked by frequency in the example.

FIG. 22 is a table showing an example of a simple scoring system for delta mass frequency analysis.

FIG. 23 is a table showing example delta mass values for certain amino acids.

FIG. 24 is a table showing delta mass frequency values for the MS/MS spectrum shown in FIG. 25.

DETAILED DESCRIPTION OF THE PREFERRED EMBODIMENT

Figure 1:
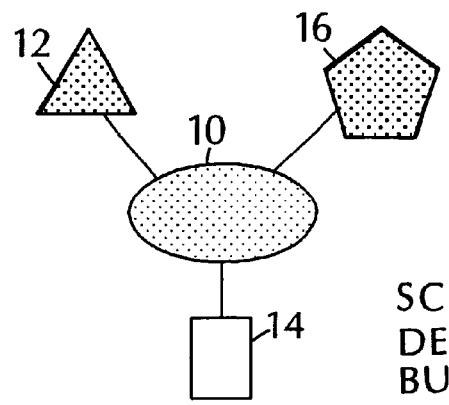
FIG. 1 is a simplified schematic diagram illustrating a molecule comprising a core structure coupled to three building blocks.

The present invention generally relates to methods for investigating relationships in chemical structure among mixtures of molecules, e.g., complex mixtures of organic molecules. Use of the invention assists in identifying unknown chemical structures that are related to one or more known structures. The relationship between known and unknown structures may be a very simple change in structure, or it may be the result of fairly complex changes in structure. The method is preferably used in conjunction with mass spectrometry (MS), an analytical technique used to investigate chemical structures.

Briefly, in accordance with the invention, the measured masses of the US members are compared with the expected masses of the DS. The mass differences between US members and DS members are compared. Rather than considering mass difference in isolation, the change in mass ($\Delta M$) between molecules is analyzed as a function dependent upon structure ($\Delta S$). The mass difference is then considered as a differential function, $\Delta M/\Delta S$, the result of which is calculated for each ion in the US when compared with each ion in the DS. These values are then correlated with values that would be expected based on assumed possible structural modifications. In addition, higher order differential functions, such as $\Delta^2 M/\Delta S^2$, can be used as needed to allow for correlation of structures in which more than one structural motif has changed.

The method steps described herein with respect to the various embodiments of the invention are preferably implemented in a general purpose computer. A representative computer is a personal computer or workstation platform that is, e.g., INTEL PENTIUM®, POWERPC®, or RISC® based, and includes an operating system such as WINDOWS®, OS/2®, Unix® or the like. As is well known, such machines include a display interface (a graphical user interface or "GUI") and associated input devices (e.g., a keyboard or mouse).

The method steps are preferably implemented in software, and accordingly one of the preferred implementations of the invention is as a set of instructions (program code) in a code module resident in the random access memory of the computer. Until required by the computer, the set of instructions may be stored in another computer memory, e.g., in a hard disk drive, or in a removable memory such as an optical disk (for eventual use in a CD ROM) or floppy disk (for eventual use in a floppy disk drive), or downloaded via the Internet or some other computer network. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the specified method steps.

The examples below generally apply to the deconvolution of mass-coded libraries, which are complex mixtures of organic molecules. However, it should be understood that the inventive process is broadly applicable to any investigation process in which molecules are related by common structural features.

A brief description is now provided of the nature of structural modification at the chemical level. Structural modifications of the type that are accounted for in accordance with the invention can be identified as being one of two types: "substitutive" and "additive".

Substitutive Modification

In substitutive modification, a part of the expected structure is replaced by an undesired structural motif. With regard to mass, the net effect is that the desired and undesired molecules differ by the difference between the substituting and substituted motifs.

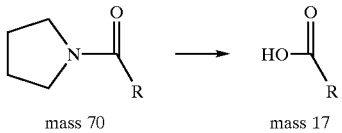

mass 70     mass 17

In the example shown above, the cyclic motif (mass 70) has been replaced by an —OH motif (mass 17), and the net difference is then 70−17=53.

Additive Modification

An additive modification occurs when an additional motif is attached to the expected structure, or when a motif that should have been removed by the chemistry in fact remains on the structure.

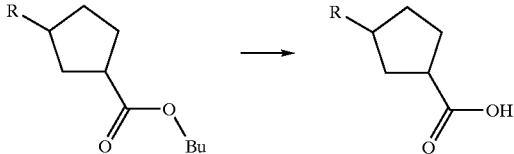

Bu=butyl M=57

In this example, a butyl-protecting group (composition $C_4H_9$) should have been removed in the course of synthesis and its position replaced with a hydrogen atom, but has in fact remained coupled to the molecule. The result is a molecule that is 56 masses higher then the desired product (structure shown at right).

This type of modification could also be considered as a variant on the substitutive process. Note that if the hydrogen atom in the place of the butyl group is viewed itself as a structural motif, then the substitution of mass 57 by mass 1 (the hydrogen's mass) gives the same net difference of 56. There are, however, disadvantages of handling this computationally as a substitutive process. Principally, doing so requires many modifications to the database of allowed BB structures to accommodate all possible substitutions. In addition, the size of the data sets that have to be generated and processed become much larger and therefore more time consuming to process. The example below shows how the addition of groups such as butyl is better handled as an additive effect, distinct from a substitutive process.

Library Quality Control Example

The following example demonstrates the application of the invention to a combinatorial library. The library under study was synthesized by the reaction of a core with four different BBs. Each product molecule contains four BBs bound to the core and all permutations and combinations of BBs around the core are possible.

FIG. 3 shows the mass information for the set of building blocks used in the generation of this library. The numbers on the vertical and horizontal axes of the table represent the building block numbers in a database of building blocks. The numbers that are italicized represent the masses of the individual building blocks. The other numbers in the table represent the difference in mass between every pair of building blocks. For example, BB 42 (mass 99) and BB 115 (mass 146) differ by 47 masses. Therefore, any pair of chemical structures that vary from each other only in substitution of one of these BBs for the other will be 47 different in mass from each other.

FIG. 4 represents a listing of all 35 molecules that should exist in this example library. The mass of each member is calculated by adding the mass of each BB to the mass of the core, which is common to all structures in the library. Every possible permutation of the four BBs in this library is shown in FIG. 4. Since the objective of the synthesis was to generate a library that contains these 35 species, this listing can be said to represent the DS of masses for this library. It follows that any other masses recorded in the study of this library represent species that do not belong to the library because all library masses are shown in FIG. 4. Therefore, any mass recorded that does not appear in this list is said to be a member of US where the US represents every mass found that does not appear in FIG. 4.

FIG. 5 shows five masses that were determined as being among the members of the US for this library. The objective for the analyst is to identify the chemical nature of these species. Unambiguous proof of structure would require purification of each member of the US, with full structural characterization of each component. The mass alone can be indicative of overall chemical formula for the ion measured if the measurement is made with sufficient accuracy. However, this method is not entirely reliable and may still result in ambiguous assignments. Furthermore, this technique provides information regarding elemental composition, but a significant amount of further work remains if one is to relate that elemental information to possible structures that may be related in some way to the DS.

A technique that allows for suggested, tentative structure assignments is more practical. The chemist would seek information as to how well the chemistry performed and, if behavior deviated dramatically from expected, some indication of what went wrong.

Accordingly, tentative structural assignments for masses in the US are preferably provided, based upon the measured mass of each ion and its relationship to the masses of the DS. The presence of the DS is needed because a measured mass is tested against the hypothetical DS structures.

The masses of the DS and US are first arranged into a two dimensional table. This is shown, e.g., in FIG. 6. The masses of the DS are shown on the vertical axis and the masses of the US are on the horizontal axis. The contents of the table reflect the difference in mass between every pair of ions made by selecting one ion from the DS and one from the US. These values are termed "delta mass values" (DMVs). The sign (positive or negative) of the DMVs is retained in this table and throughout each calculation that follows.

The next step involves making some assumptions regarding the errors in chemistry (substitutions and/or additions) that might occur, resulting in generation of the molecules that belong to the US. In this illustration, two assumptions are made. First, it is assumed that the only allowed substitution that might occur is replacement of a building block with a hydroxyl group. Second, it is assumed that the only addition that might occur is the butyl group, and that as many as three butyl groups may have been retained. (These assumptions can be based, e.g., on the propensity of a species to undergo a hydrolysis step (replacement of a moiety by an —OH group) and the propensity of a protected species to retain the protecting group when it should be removed as routinely observed in chemistry laboratories. It should be noted that the assumptions do not necessarily have to be routinely observed, but can be merely possible. For example, general questions, such as "did the solvent used in this reaction play an unexpectedly reactive role" can be tested, with no prior experience of such a reaction occurring.)

The method proceeds by calculating the effects that each allowed addition and/or substitution would have on the masses of the DS. In other words, the mass of each member of the DS will be displaced by some predictable amount by each allowed substitution and addition, and the predicted shift in mass can be calculated.

First, the shift of allowed additions is calculated. FIG. 7 shows the net mass displacement for any member of the DS resulting from the addition of one through three butyl groups.

The next step is to take FIG. 3 and expand it to include all of the motifs allowed as substitutions. In this case, the hydroxyl group, mass 17, is the only substitution allowed, and so this is the only addition to the table. The result is shown in FIG. 8. Next, the net effect of each allowed addition to the values in FIG. 8 is computed and tabulated. The result is shown in FIG. 9, which shows the net effect of a —OH substitution and the addition of one through three butyl groups.

FIGS. 7 through 9 represent changes in mass ($\Delta M$) resulting from changes in structure ($\Delta S$) for all possible structural changes. These tables can be thought of in the context of differential calculus as representing $\Delta M/\Delta S$, i.e., the change in mass as a function of the change in structure, for the allowed structures and all permitted hypothetical modifications.

Zero Order Considerations (Additions, No Substitutions)

An attempt can now be made to correlate US members with DS structures. First, the mass shifts that result from allowed additions are considered, assuming no substitutions have occurred. This is referred to as a "zero order change", where the zero indicates the fact that no substitution has occurred.

FIG. 6 is duplicated in FIG. 10, but the DMVs that are co-incident between FIG. 6 and FIG. 7 are highlighted. In the column corresponding to mass 994 in Table 8, the value of 112 is indicated as the only value to appear in both FIGS. 6 and 7. This coincidence suggests that mass 994 could be the result of the addition of 2 butyl groups to mass 882. Inspection of FIG. 4 reveals the composition of mass 882 (115, 115, 307, 307), as the structure to which the hypothetical addition occurred, and therefore it is determined that it is this structure modified by the addition of 2 butyl groups that is responsible for the mass 994 species.

Inspection of the column for mass 956 in FIG. 10 reveals 3 co-incidences with FIG. 7. The observed mass is 56 higher than mass 900 (one butyl group addition) and is 168 masses higher than mass 788 (three butyl groups). There are two library members at mass 788. Within the scope of the invention as described here, any one of these explanations is possible, or the 956 mass could be the result of all three modifications. Some intelligent interpretation might however be possible to reduce the number of possibilities from consideration. For example, a determination could be made as to whether the library members at mass 788 have compositions will allow for the addition of three butyl groups. If this is not possible, then this possibility is eliminated.

The remaining four ions (606, 612, 742, 640) in FIG. 6 have no co-incidences with FIG. 10, which reveals that these masses cannot be explained in terms of simple addition of butyl groups to the DS.

First Order Changes (One Substitution, with or without Additions)

The next step is to consider the possibilities that occur when a single substitution is allowed, i.e., a first order change. Evaluation proceeds by comparing the values contained in FIG. 8 with the columns of FIG. 6. The summary of this comparison is shown in FIG. 11, with the co-incident delta masses highlighted.

The columns of FIG. 11 are examined in order. First, the column for Mass 606 has no co-incidences. This reveals that 606 cannot arise as a consequence of any allowed single substitution. Mass 612 has four co-incident values. This serves as a positive identification for single substitution because there are four ways in which mass 612 might have arisen by substitution of an —OH group for one of the BBs as shown in FIG. 2.

Figure 2:
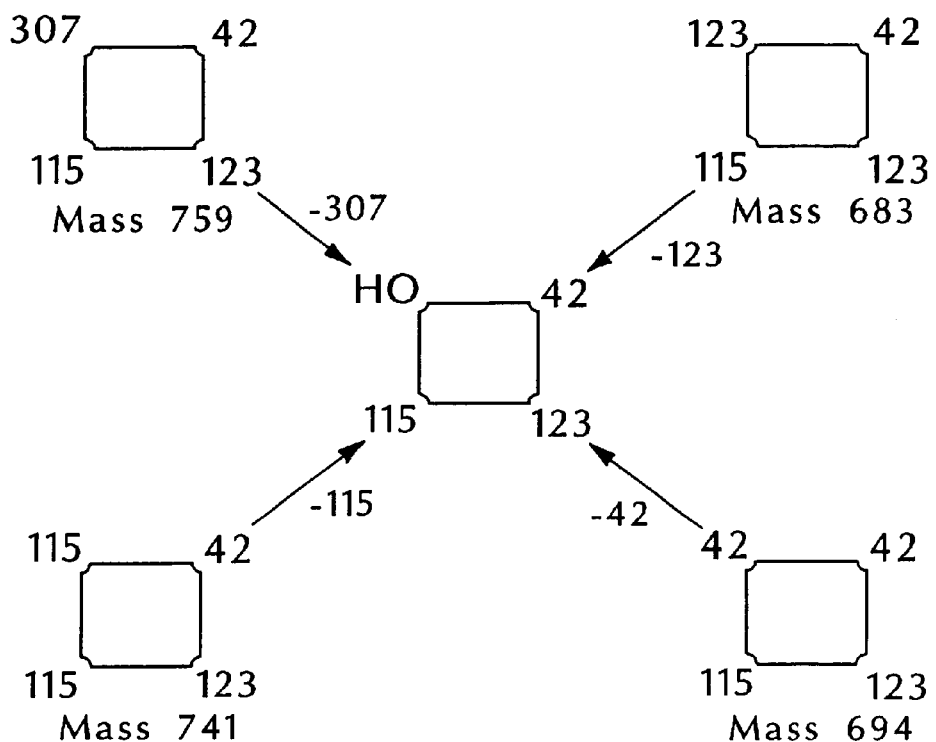
FIG. 2 is a schematic diagram illustrating multiple possible substitutions to produce a given mass.

FIG. 2 illustrates that any one BB might be substituted by —OH to give the molecule with mass 612. It is significant to note that the number of single substitutions that can give rise to a common product is equal to the number of BBs used in the synthesis. For example, if eight BBs had been used in the synthesis then there would have been eight substitutions in the manner shown above that would yield mass 612 as the product. A first general rule applied to this embodiment of the invention can therefore be stated as follows: Any single substitution will be identified in the first order substitution delta mass tables by a number of co-incidences equal to the number of structural motifs (building blocks) used in the generation of the desired set. This can be represented as follows:

$$Nc_1 = N_m$$

where $Nc_1$=number of co-incidences at the first order of substitution

Nm=The number of building block motifs used in the synthesis.

This observation on the number of co-incidences is a particularly useful, because it immediately allows an analyst to discount occasional serendipitous co-incidences. There are other masses highlighted in FIG. 11, e.g., that show a single co-incidence. Consider two of them, 742 ($\Delta M = -82$) and 994 ($\Delta M = 76$). These cannot be indicators of substitution because the single occurrence in each column contravenes the first rule stated above. Closer inspection of each single incidence reveals why the substitutions suggested by the delta mass values cannot be genuine. First, mass 742 is 82 lower than 824. FIG. 4 shows that the BB composition of mass 824 is (115, 123, 307, 307), while FIG. 7 shows that a −82 delta mass corresponds to the substitution of BB 42 by an —OH group. However, the library compound of mass 824 does not contain any BB 42 and so such a substitution is impossible in the context of this library member.

Similarly, mass 994 is 76 masses higher than library member 918. The composition of 918 is (307, 307, 307, 307), while a delta mass of 76 is suggestive of a substitution of BB123 by BB307. Since mass 918 contains no BB123, such a substitution is impossible. Therefore the first rule is helpful because it eliminates the need to check comparisons of structures that serendipitously coincide with one or two delta mass values, but in reality can have no structural correlation. Only occurrences with frequency demanded by the first rule should even be considered.

FIG. 8 contains all of the DMVs that are co-incident with a possible substitution of all BBs and substitutions (the hydroxyl group in this case). In reality, it is only necessary to draw up the delta mass table to reflect the differences between the substituting motif(s) and the allowed building blocks, since the substitutions obtained by swapping one BB for another are all accounted for in the DS. If more than one substituting motif is to be considered, those too must be included. However, for clarity of illustration, all values have been included here in FIG. 8.

Next, the possibility is considered that a mass in the US might result from both substitution and addition. This is tested by generating a table that reflects the amount that each permitted addition displaces the $\Delta M/\Delta S$ values in FIG. 8. FIG. 9 shows the effect of adding 1, 2 and 3 butyl groups on the values of FIG. 8 that involve the allowed substitution. A comparison of FIG. 9 with the masses in FIG. 6 is performed and the results are summarized in FIG. 12, with co-incident values highlighted. Note that four of the values for 2 butyl groups in FIG. 12 are co-incident with values in the column corresponding to mass 742. This is suggestive of structural inference, since the number of co-incidences is consistent with the first rule. Note that additions have no effect on the number of co-incidences demanded by the first rule, the application of the rule is determined only by the order of substitution. Additions with zero substitutions have no defined rule of co-incidence.

There is also one other co-incidence in FIG. 12; mass 612 has a value −35, which is one of the values for 2 butyl additions. However, this is a single co-incidence and therefore can be eliminated as a possible structural inference by the first rule.

Second Order Changes (Two Substitutions with or without Additions)

It is possible that members of the US might arise as the result of multiple failures in the desired chemistry. The correlation of these compounds with the DS will not be achieved with the comparisons performed thus far. The net difference in masses between members of the DS and structures resulting from a total of two substitutions will be indicated by the sum of the delta masses for each substitution that has occurred.

Such second order structural changes can be considered to be "the difference between the difference between the masses" or as a second order differential function D2M/DS2. In accordance with a further embodiment of the invention, such second order changes are determined using a second order delta mass table. The values in the body of the first order delta mass table (FIG. 8) that pertain to an allowed substitution are themselves arranged along the axes of a new table. The body of this new table (FIG. 13) then contains the values that correspond to the difference in masses between the first order differences in masses. A similar table, accounting for the effects of butyl additions to this set is generated and shown in FIGURE 14. FIGS. 13 AND 14 can now be compared with the DMVs in FIG. 6 to search for correlation.

Results of the comparison are summarized in FIG. 15. Inspection reveals that there are 10 values found in the column for mass 606 that correspond to values in FIG. 13. This frequency is indicative of a second order correlation, because there are 10 possible double substitutions to the DS of masses that will result in generation of a structure with mass 606 containing two hydroxyl substitutions. Expressed mathematically, calculating the sigma value for the number of BBs used in the library generation will indicate the number of delta mass correlations that will occur for a second order substitution. In this example, four BBs were used, so the number of correlations will be 1+2+3+4=10.

This leads to the second general rule in accordance with this embodiment of the invention: Any double substitution will be identified in the second order substitution delta mass tables ($^2S/M^2$) by a number of co-incidences equal to the mathematical expression sigma 1 to n, where n equals the number of motifs (building blocks) used in the generation of the desired set. This can be expressed mathematically as follows:

$$Nc_2 = \Sigma N_m$$

Where $Nc_2$=number of co-incidences at the second order of substitution

Nm=The number of building block motifs used in the synthesis.

FIG. 16 summarizes the results of comparing the butyl addition (FIG. 14). There are 10 co-incidences under mass 640 co-incident with values in the third column of FIG. 14, suggesting that mass 640 is the result of 2 allowed substitutions and the addition of 3 butyl groups. Once again, the frequency of co-incidence is determined by the second order rule.

Higher Order Considerations

All of the ions set out in FIG. 5 now have tentative structures assigned to them in accordance with the invention. FIG. 17 shows a summary of the assignments made. There may be incidences in which ions remain unassigned at this point. In accordance with a further embodiment of the invention, it is possible to test for further substitution. The method above describes the process by which first order $\Delta S/\Delta M$ values are processed to generate second order $\Delta 2S/\Delta M2$ values. That process may be further extended, taking the second order values on to the axes of a new table and generating a third order table, $\Delta 3 S/\Delta M3$, and so on. Each subsequent differential will have its own predictable number of co-incidences, and any match observed must have that number of co-incidences to represent a valid interpretation at that level of substitution. Theoretically, this process can be extended to any degree desired.

The process for ion structure assignment is generally summarized as follows for the example described above:
1. Generate a list of all detected masses in a run, allowing for isotope correction and charge state identification, as described in, e.g., U.S. Pat. No. 6,207,861 issued to Nash et al.
2. Generate a list of all masses that belong to the desired set.
3. Generate a table showing the displacement of masses in the desired set caused by any allowed additional groups.
4. Generate a delta mass table from the list of desired structural motifs and any allowed substitutions.
5. Generate a delta mass table showing the displacement of the values from Step 4 caused by any allowed additional groups.
6. Segregate the detected mass peak list into two separate lists, according to whether each peak is an expected library mass (a member of the DS) or not a library mass (the US).

7. Generate a mass difference table from the masses of the desired set and the detected list of US masses, with each column containing the mass differences for one US member.
8. Compare the list from Step 7 with the table of mass shifts caused by addition (table in step 3).
9. Report correlations found in Step 7.
10. Compare the list from Step 7 with the values generated for the substitutions in Step 4.
11. Report any matches that obey Rule 1, i.e. the number of coincidences that appear in any column from Step 3 is equal to the number of motifs used in the synthesis.
12. Compare values from Step 7 with values from Step 5.
13. Report any column showing a co-incidence frequency consistent with Rule 1.
14. If desired, generate second order tables.
15. Compare the values from Step 7 with the values in Step 14.
16. Report any column showing a coincident frequency consistent with Rule 2.
17. Generate a table showing the displacement on the masses from Step 14 caused by allowed additions.
18. Compare the values from Step 7 with the values from Step 17.
19. Report any column showing a coincident frequency consistent with Rule 2.
20. Repeat Steps 14 to 19 to the desired order of substitution.

Delta Mass Frequency Analysis for Refractory Situations

The method described above will lead to successful indications of possible structures for the US in any case, in any system, so long as two criteria are met: the theoretical composition of the DS is known and the correct assumptions are made regarding allowed substitution and addition. In cases where an analyst is unable to find hypothetical interpretations, one of two explanations is likely. The first explanation is that many members of the US are in reality structurally unrelated to the DS in any meaningful way. In a drug discovery application, this is generally unlikely. However, when broader applications are considered, the possibility of this is greater. The second explanation is that the two sets are related, but the analyst has failed to identify the nature of the substitution that has occurred and is therefore unable to find correlation because he or she is not allowing appropriate substitution and/or addition masses in the delta mass tables. It is important to differentiate between these two explanations because the substitution of an unidentified motif derived from the chemical system (such as solvents) will make repetitive failure of the chemistry more likely if it is not identified and controlled.

One approach to solving this problem is to calculate the delta mass tables repetitively, and increment the mass of the substitution at each iteration. In this way, one might hope to at least identify the net mass difference involved and thereby the mass of the substituting motif. However, this approach is inadequate in several ways. It may be relatively time consuming to perform, particularly when high mass accuracy numbers are considered. The number that represents the net mass difference does not immediately identify the nature of the motifs responsible, and there is no guarantee of success, because there is no certainty that the two sets of masses are correlated in the first place.

In such highly complex situations, where attempts to correlate based on assumed types of change have failed, a method is needed that allows the operator to compare the relationship of the masses within the DS and also to compare the relationship of the masses within the US and to determine if there are some characteristics common to both sets. If such a correlation exists, then it is worth pursuing the incremental mass approach outlined above. If there is no correlation, then the approach will not work because if the masses are generally non-correlated, the method is not able to identify structures anyway.

The theory behind this approach is that if the US is the result of some modification to the structures of the DS, then some of the intraset DMVs will be common to both sets. The approach to this analysis is to look at the mass differences between intraset members and to look at the frequencies with which each mass difference occurs. For example, consider again the DS of masses shown in FIG. 4. First, these masses are arranged into a 2 dimensional table, in the style of FIG. 6, but now the masses of the DS lie along both axes of the table, and the table values now reflect the difference in mass between every pair of masses in the DS. Next, a frequency analysis is performed on this table, to determine how frequently each mass difference occurs. The results of such an analysis for this library is shown in FIG. 18. This type of table is identified herein as a delta mass frequency table (DMF table).

Now, suppose that the chemist who made this library had inadvertently included a second core motif with a different mass to the core for the DS. If the chemistry worked without failure on both core motifs, the result would be that there would be present an US of molecules whose masses would be displaced from each other by exactly the same spacing as for the DS, and from those of the DS by the difference in mass between the two core motifs. However, when these two sets of ions are listed separately and a DMF table drawn up for each of the two sets, the contents of the two DMF tables will be identical, irrespective of the mass difference between the two core motifs. This shows that a level of correlation between the US and the DS can be achieved without necessarily comparing their values to each other. Therefore, it will be generally true that DMF tables for any DS and US will show a high degree of correlation for instances in which the two sets are structurally related and will show very little correlation in cases where this is little or no structural correlation between the sets.

As an example, consider the list of ions shown in FIG. 19. These ions are some members of the US discovered empirically during QC analysis of the example library. These ions are all higher in mass than the highest mass library member. Therefore, if they are identifiers for structurally related compounds, these compounds must be either the product of substitution involving a motif larger than any of the BBs used, or else the product of some addition, or both.

The DMF table for the US (the ions in FIG. 19) is produced in a similar manner to the DMF table for the DS and is shown in FIG. 20. These two DMF tables can then be sorted according to the frequency values in each table. The two tables, sorted in this manner, are shown in FIG. 21. The next step is to perform a comparison of the two tables. Delta mass values that appear with high frequency in both tables are assigned a high score, while a delta mass value that appears with high frequency in the US but low frequency (or not at all) in the DS is assigned a low value.

There is one further level of complexity in this scoring process. In this example, many of the high frequency DMVs in the US have no match in the DS, e.g., DMV 56 in the US. We know that this value corresponds to the mass of a butyl group addition. Recall that the values in this DMV table are making a comparison of all members of the US. Since butyl is not a substitutive motif in the DS, 56 cannot appear in the DMF table for the DS. However, among the members of the US, any DMV is possible. If two members of the US differ from each other by the addition of a butyl group, then a DMV of 56 will appear. This is in itself useful information, but is not useful if it is used to assign a low score to the comparison described above.

In order to accommodate such differences, a rule in accordance with this embodiment of the invention states that any of the allowed additions described in FIG. 7 are also allowed in comparison of DMF tables. The process of doing so proceeds by considering only those members of the US that did not match in the first pass, described above. Each of the unscored values is taken and adjusted to compensate for the effect of the hypothetical addition(s). This adjustment is performed by first comparing the number directly to the values that correspond to the effects of addition. In this example, 56 and 112 will score, because these values correspond to the addition of one and two butyl groups, respectively. If no match is found, then the DMV under consideration is adjusted to account for the possibility that it is itself the result of both an addition and a substitution. The DMV is first adjusted by adding the mass of the allowed addition and testing again against the DMF table for the DS. Then the same original value is tested again by subtracting it from the mass of the allowed addition and testing once more against the DMF table for the DS.

For example, the DMV 38 appears in the DMF table for the US. This value did not correlate with any member of the DMF table for the DS in the first pass. If the mass of butyl is added to this value, the result is (38+56=) 94. Similarly, if the subtractive calculation is performed, the result is (56−38=) 18. Both of these new values appear as high frequency occurrences in the DMF table for the DS, and therefore the score for the DMV 38 is adjusted to show correlation at an appropriate level.

This process is performed for each mass that was unmatched in the first pass. The results of both the first pass and the second pass are then reported. FIG. 22 shows the results using an arbitrary correlation scoring method. These results taken together are of value for the following reasons. A good correlation on the first pass indicates that the US of ions is structurally related to the DS. A low score suggests there is little correlation. If the two scores reported are of similar or identical values, then this indicates that addition of the allowed motifs is unlikely to explain the relationship of the US, and consequently is unlikely to explain the relationship between the US and the DS. Finally, if the score on the second pass is significantly better than the score on the first pass, this indicates that additional masses have been identified as possibly explained by allowed addition. Such an observation further suggests that differences between the US and DS will be similarly explained.

The DMF process is generally summarized as follows:

1. Calculate a delta mass table using the hypothetical masses of the DS along both axes.
2. Generate a delta mass table using the measured masses of the US along both axes.
3. Generate a DMF table for the DS from the values generated in Step 1.
4. Generate a DMF table for the US from the values generated in Step 2.
5. Rank the values generated in Step 3 in order of frequency
6. Rank the values generated in Step 4 in order of frequency.
7. For each mass value ranked in Step 6 compare with the mass values ranked in Step 5.
8. Assign a suitable scoring system to the comparisons in 7. High frequency values with co-incident delta masses have a high likelihood of correlation, high frequency delta mass for the US that have no match in the DS have a low likelihood of correlation.
9. Repeat Step 8, adjusting plus and minus for any allowed additional motifs, as necessary.
10. Report the scores from Steps 8 and 9 (if performed).
11. If correlation meets a user defined value, then perform search for allowed substitutions and additions as indicated in Steps 12–19 below.
12. Generate a delta mass table for the building block motifs and one hypothetical substitution, whose mass is assigned a chosen minimum value.
13. Generate a mass difference table from the masses of the desired set and the detected list of US masses, with each column containing the mass differences for one US member.
14. Compare the substituting values from Step 12 with the delta mass values from Step 13.
15. Report incident values whose frequency is consistent with the first order rule of substitution, together with the substitution mass value.
16. Increment the substitution value in Step 12 at a chosen granularity and regenerate the table from Step 12 to reflect this new value.
17. Compare the values from Step 13 with the values from Step 16.
18. Report incident values whose frequency is consistent with the first order rule of substitution, along with the substitution mass value.
19. Repeat Steps 16 to 19 until the maximum chosen mass for the substitution block.

Use of High Mass Accuracy

In all of the examples described above, the masses have been reported to the integer mass value. Recording masses to this level of accuracy is within the realm of typically every mass spectrometer in use today recording data of this type. There is also, however, a subset of instruments that are capable of recording to a much higher degree of accuracy. Examples of such instruments are those based upon Ion Cyclotron Resonance detection such as, e.g., the model Apex III from Bruker Daltonics, Billerica, Mass. See www-.daltonics.bruker.com. Other instruments can be based upon Time-of-flight detection such as, e.g., the model LCT instrument from Micromass Instruments, Beverly, Mass. See www.micromass.co.uk. Finally, less-common magnetic sector instruments are also capable of high accuracy mass measurements, e.g., the model "LCMate" from JEOL USA, Inc., Peabody, Mass. See www.jeol.com/ms/ms.html. At the practical level, the type of accuracy that may be obtained routinely is at least as good as +/−0.030 of the actual mass of the ion species. This is particularly valuable when attempting to differentiate between species that have the same integer mass, but different masses at the fractional mass level. A simple example of this can be drawn from the field of gas analysis. Consider three common gaseous compounds: carbon monoxide (CO), nitrogen ($N_2$) and ethylene ($C_2H_4$), either of which have mass 28 at the integer level. If an instrument measuring these gases were only capable of measurements at the integer mass level then it would be impossible to distinguish between them. However, at the fractional mass level, carbon monoxide has a mass of 27.9949, nitrogen has a mass of 28.0060 and ethylene has a mass of 28.0313. Therefore, an instrument capable of measurement to the high millimass level of accuracy (1 millimass=0.001 mass) could distinguish between these species.

In the context of the invention, data accurate to the millimass level of accuracy is particularly useful. In FIG. 4 there are two entries at mass 788. In fact, these entries have masses 788.3578 and 788.2069, and have a difference of 0.1509 masses. Therefore, when any of the delta mass values relating to either of these species are considered at the integer mass level, the species are indistinct and the interpretations ambiguous. However, when considered at the fractional mass level, with appropriate tolerances set to allow for small errors in practical mass measurement, the species become distinct. In conclusion, while the invention can be used to solve problems at integer mass resolution, data acquired with greater mass accuracy will generally afford less ambiguous structural assignments.

Data collected at high mass accuracy can be used to perform a further check on the assigned theoretical compositions. It is well known in the art that measurements to the third and fourth decimal place may be used to generate a list of possible elemental compositions for a mass. With measurements made to this level of accuracy, the measured mass of an ion in the US can be compared with the calculated mass of any structure assigned as a possible explanation for the ion. If the expected error window in the measurement of the mass is known, then the difference between the calculated mass of the assigned structure and the measured mass gives a further indication as to the likelihood that the interpretation is correct.

The various embodiments of the invention described above provide a number of advantages. First, they generally permit large numbers of masses in the US to be handled simultaneously. Second, large numbers of allowed substitutions and additions can generally be handled, allowing even highly unlikely events to be checked.

Furthermore, the described methods are broadly applicable to any system in which some structures are known and some are generally unknown. For example, in the case of peptide studies, mutation sometimes causes the sequence of a protein to be changed. If the sequence is known prior to mutation to produce a signal of mass x, which disappears after mutation, and if a signal with mass y appears after mutation that was not evident before mutation, then it is reasonable to assume that the mass shift (x-y) is a consequence of mutation. The method might then be exploited to list all likely structure changes to the peptide that would explain the quantity (x-y). Note that in this particular example, the DS and US each have a single member.

Other Applications

In addition to the examples described above, the present invention can be applied to a variety of cases in which a number of predicted masses making up a DS of molecules are accompanied by an US of masses, some or all of which are the result of structural modification to some member of the DS. Particular areas in which the invention can be applied include the following:

1. Peptide and Protein Chemistry

Determining the sequence of peptide chains is of major importance is the study of proteomics and drug discovery. Peptides are made of chains of amino acids. Determining the sequence of the amino acids in the chains is of great interest in the areas of proteomics and protein structure determination. Sequences sometimes have a significant degree of homology, but may differ by a small part of their sequence.

A method in accordance with the invention could be used to investigate likely changes in sequence that result in a mass shift. In the case of peptides, a substitutive change would be the swapping of any amino acid for any other amino acid. In this case, the DS is merely the mass of the known peptide sequence, and any amino acid becomes an allowed substitution for any other. While this may appear to add a level of complexity, in fact the delta mass table is always the same. FIG. 23 shows the delta mass table that would be used for all of the amino acids that occur in animal systems.

An additive change in peptide chemistry might be a post-translational modification, such as the addition of a phosphate moiety to a residue, which would add a mass of 80. Most common additions are known and would be arranged in to a standard set of additions.

2. Metabolic Studies

In metabolic studies, one is interested in identifying the presence of a drug molecule in a complex matrix, usually blood plasma or urine. In addition, one also seeks to identify changes that have occurred to the drug's chemical structure as a result of the organism's metabolism of the drug. Many of the changes that occur to the drug are observed empirically to be common metabolic pathways. For example, the addition of oxygen (+16) is a common pathway. In this case, the list of DS masses would be set to the masses of the target compounds and the addition and substitution lists would include all commonly mass modifiers, as appropriate. The present invention is broadly applicable in this area, and is particularly useful in cases when targets are molecules from screening that have entered clinical studies as described in the previously mentioned U.S. Pat. No. 6,207,861.

3. MS/MS

Mass spectrometry/mass spectrometry (MS/MS) is an extension of the mass spectrometric technique. It is used to study the fragmentation of ions chosen by the operator to be of interest. In brief, an ion of interest is selected as the parent ion and all other ions are rejected. The chosen parent is then induced to fragment by collision with a gas and then the masses of the fragments are recorded. Sometimes MS/MS spectra are simple and interpretation is easy, but some spectra are highly complex and interpretation is difficult.

In a MS/MS spectrum, all of the signals observed must be derived from the chosen parent ion, because this is the only ion allowed to undergo fragmentation. Therefore, all ions in the MS/MS spectrum must be structurally related, no matter how complex the interpretation becomes.

Figure 25:
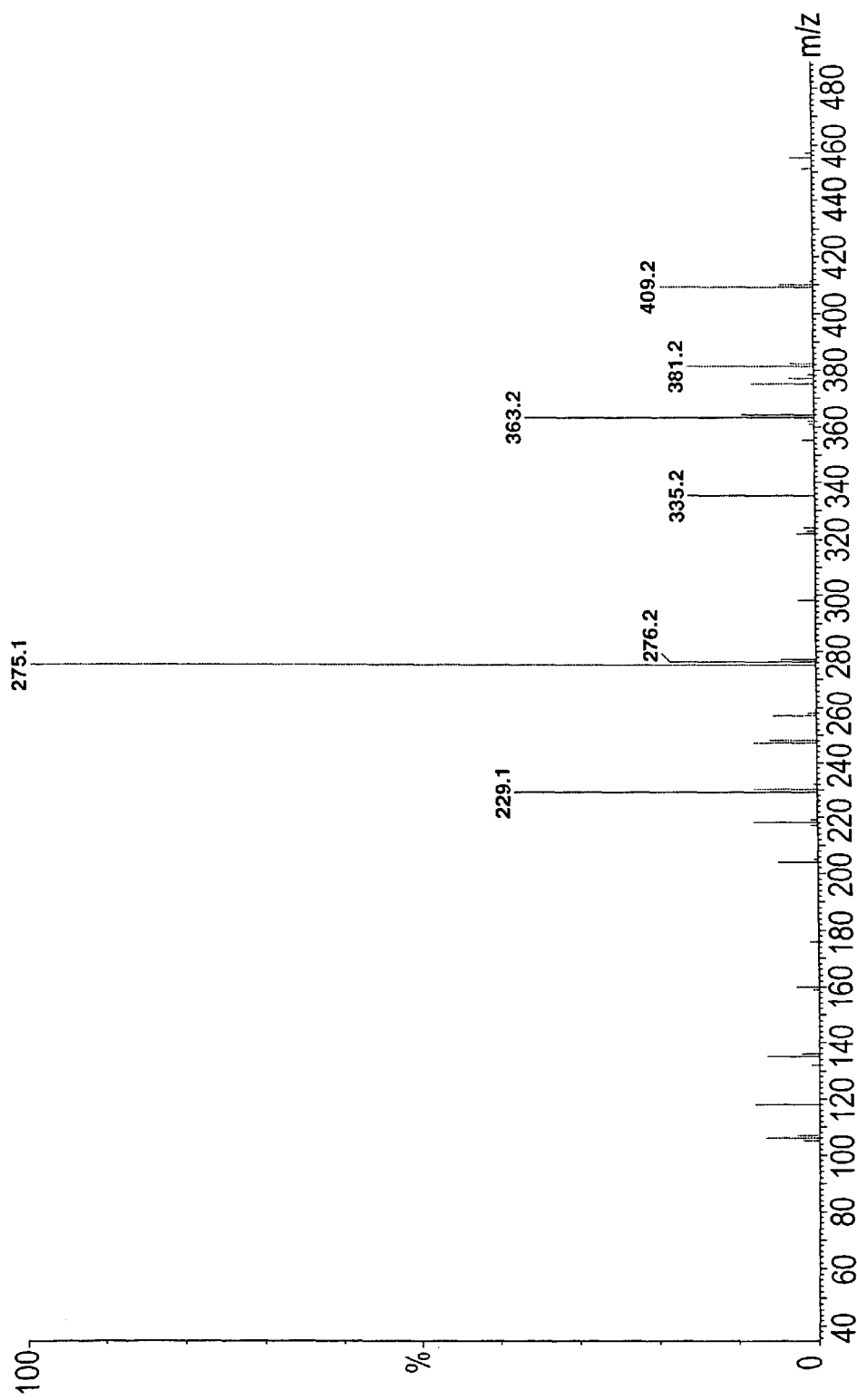
FIG. 25 is a schematic illustration of an example MS/MS mass spectrum of a molecule.

FIG. 25 shows a MS/MS mass spectrum of a molecule. In this case the mass of the selected ion was 480, which is known to be the molecular signal for the chosen molecule, and all of the lighter ions are therefore fragments. In this respect they are all members of the "desired set", where the desired set is defined as any ion that is a fragment of a chosen parent ion.

This spectrum is generally quite complex. There are typically a number of large ions observed, and the relationship between them is unclear from simple observation. Some may be the result of complex, multi-step fragmentation pathways. However, it is known that they are all structurally related in some way because they all evolved from a common parent ion.

In this example, it is known that the structure involves a tricore species, i.e., a core with 3 BBs coupled to it. FIG. 24 shows how an embodiment of the invention can be applied to MS/MS data. All of the observed ions with major intensity are arranged into a delta mass table to reveal the mass difference between each pair of ions in the mass spectrum. It is known that certain DMVs (18, 28, 46) are commonly observed, identifying the loss of water, carbon monoxide and formic acid, respectively. In this case it is also known that mass 71 is an indicator for one of the BBs used in the synthesis and that 134 and 151 are both indicators of a different BB. In the table, the DMVs that correspond to such losses are highlighted. By using these values, pairs of fragment ions may be correlated and ion structures inferred. For example, The DMV at the intersection of 275 and 409 shows a DMV of 134. This suggests that 275 was evolved by the loss of the known building block from 409.

When this approach is followed for each highlighted DMV, it emerges that for the eighteen ions listed, interpretation is immediately inferred for ten (shown in blue on the vertical axis). Of the remainder, four can be assigned a structural relationship to each other (shown in green on the vertical axis), based on the mass difference between them, even though no absolute structure is assigned. The advantage of using the invention in the MS/MS context is that it enables faster and potentially automated interpretation of the data. These spectra can take many hours to interpret manually.

The process as applied to the MS/MS example is generally summarized as follows:
1. Record mass spectrum.
2. Establish a list of possible DMV values.
3. Remove the isotope peaks, as per previous patent, from the list of masses.
4. Arrange de-isotoped signals into a DMV table (FIG. 24).
5. Inspect DMV table for coincidence with the list in FIG. 4.
6. Search table columns from left-to-right to identify co-incident pairs. Report all ions linked by coincidence.
7. Search the identified pairs for commonalties. For example, 480 and 409 are linked by DMV 71, while 409 and 363 are linked by DMV 46. In this case, 409 is a commonality and via this, 480 and 363 are also linked. Report all linked ions.
8. Report identified pairs unlinked by commonalties.
9. Report all ions not identified by the DMV table.

Other Embodiments

In accordance with an alternative embodiment of the invention, the list of allowed structural motifs is expanded to include all alternative structural modifications considered possible. For example, the motif —OH could be included as an additional motif in the list of building blocks allowed in the generation of the DS. Additionally, motifs that have the potential to include protecting groups in their final structure should be included in both the protected and deprotected forms. A protecting group is a chemical moiety that serves to prevent chemical reaction occurring at a particular site in the molecule while reactions occur at some other site in the same molecule, but can also be removed easily at a later time to allow for further reaction at the site that was being protected. Some motifs begin a synthesis with more than one protecting group. Such a structure should be entered into the motif list in four forms; (i) the desired form, (ii) the form that contains one protecting group, (iii) the form that contains only the second protecting group, if this group has a different mass to the first protecting group, and (iv) the form containing both protecting groups. The effect of this approach is to expand the DS to embrace compositions that include allowed substitutions and additions.

Having described preferred embodiments of the present invention, it should be apparent that modifications can be made without departing from the spirit and scope of the invention.

I claim:
1. A method of identifying an unknown chemical structure related to at least one known chemical structure of a plurality of known chemical structures, each of the known chemical structures comprising a core coupled with a predetermined number of building blocks, the method comprising:
   (a) identifying the chemical structures of the plurality of known chemical structures and the masses of the plurality of known chemical structures;
   (b) determining the mass of the unknown chemical structure;
   (c) calculating mass differences between the mass of the unknown chemical structure and each of the known chemical structures;
   (d) selecting a hypothetical substitutive structure;
   (e) determining expected mass displacements caused by substitution of the hypothetical substitutive structure for each building block of each of the known chemical structures;
   (f) identifying expected mass displacements equal to a mass difference calculated in step (c);
   (g) of the expected mass displacements identified as being equal to a mass difference, identifying an unknown chemical structure mass associated with the same number of identified expected mass displacements as the predetermined number of building blocks;
   (h) for the unknown chemical structure mass identified in step (g), identifying an associated known chemical structure; and
   (i) for the associated known chemical structure identified in step (h), replacing a selected building block with the hypothetical substitutive structure to form a hypothetical associated chemical structure, such that the mass of the associated known chemical structure equals the mass of the unknown chemical structure, said hypothetical associated chemical structure comprising the unknown chemical structure.

2. The method of claim 1 wherein the masses of the known and unknown chemical structures are obtained using mass spectrometry.

3. The method of claim 1 wherein step (c) comprises generating a mass difference table from the masses of the known chemical structures and the unknown chemical structure.

4. The method of claim 1 wherein said plurality of known chemical structures comprises a combinatorial library.

5. The method of claim 1 wherein at least some steps are implemented in a computer.

6. The method of claim 1 wherein steps (b), (c), and (e) are implemented in a computer.

7. The method of claim 1 wherein steps (a)-(i) are implemented in a computer.

8. A method of identifying an unknown chemical structure related to at least one known chemical structure of a plurality of known chemical structures, each of the known chemical structures comprising a core coupled with a predetermined number of building blocks, the method comprising:
   (a) identifying the chemical structures masses of the plurality of known chemical structures and the masses of the plurality of known chemical structures;
   (b) determining the mass of the unknown chemical structure;
   (c) calculating mass differences between the mass of the unknown chemical structure and each of the known chemical structures;

(d) selecting a hypothetical substitutive structure;
(e) determining expected mass displacements caused by substitution of the hypothetical substitutive structure for each building block of each of the known chemical structures;
(f) selecting a hypothetical additive structure;
(g) determining expected mass displacements caused by addition of the hypothetical additive structure to the expected mass displacements determined in step (e);
(h) identifying expected mass displacements determined in step (g) equal to a mass difference calculated in step (c);
(i) of the expected mass displacements identified as being equal to a mass difference, identifying an unknown chemical structure mass associated with the same number of identified expected mass displacements as the predetermined number of building blocks;
(j) for the unknown chemical structure mass identified in step (i), identifying an associated known chemical structure; and
(k) for the associated known chemical structure identified in step (j), adding the hypothetical additive structure and replacing a selected building block with the hypothetical substitutive structure to form a hypothetical associated chemical structure, such that the mass of the associated known chemical structure equals the mass of the unknown chemical structure, said hypothetical associated chemical structure comprising the unknown chemical structure.

9. The method of claim 8 wherein the masses of the known and unknown chemical structures are obtained using mass spectrometry.

10. The method of claim 8 wherein step (c) comprises generating a mass difference table from the masses of the k known chemical structures and the unknown chemical structure.

11. The method of claim 8 wherein said plurality of known chemical structures comprises a combinatorial library.

12. A method of identifying an unknown chemical structure related to at least one known chemical structure of a plurality of known chemical structures, each of the known chemical structures comprising a core coupled with a predetermined number of building blocks, the method comprising:
(a) identifying the chemical structures of the plurality of known chemical structures and the masses of the plurality of known chemical structures;
(b) determining the mass of the unknown chemical structure;
(c) calculating mass differences between the mass of the unknown chemical structure and each of the known chemical structures;
(d) selecting a hypothetical substitutive structure;
(e) determining expected mass displacements caused by substitution of the hypothetical substitutive structure for each building block of each of the known chemical structures;
(f) determining the differences between the expected mass displacements determined in step (e);
(g) identifying differences determined in step (f) equal to a mass difference determined in step (c);
(h) of the differences identified in step (g), identifying an unknown chemical structure mass associated with the same number of differences as the sigma value for the predetermined number of building blocks;
(i) for the unknown chemical structure mass identified in step (h), identifying an associated known chemical structure; and
(j) for the associated known chemical structure identified in step (i), replacing two selected building blocks with the hypothetical substitutive structure to form a hypothetical associated chemical structure, such that the mass of the associated known chemical structure equals the mass of the unknown chemical structure, said hypothetical associated chemical structure comprising the unknown chemical structure.

13. The method of claim 12, wherein the sigma value is determined by the mathematical expression sigma 1 to N, where N is the number of building blocks.

14. The method of claim 12 wherein the masses of the known and unknown chemical structures are obtained using m ass spectrometry.

15. The method of claim 12 wherein step (c) comprises generating a mass difference table from the masses of the plurality of known chemical structures and the unknown chemical structure.

16. The method of claim 12 wherein said plurality of known chemical structures comprises a combinatorial library.

17. The method of claim 12 wherein at least some steps are implemented in a computer.

18. The method of claim 12 wherein steps (b), (c), (e), (f), and (j) are implemented in a computer.

19. The method of claim 12 wherein steps (a)-(j) are implemented in a computer.

20. A method of identifying an unknown chemical structure related to at least one known chemical structure of a plurality of known chemical structures, each of the known chemical structures comprising a core coupled with a predetermined number of building blocks, the method comprising:
(a) identifying the chemical structures of the plurality of known chemical structures and the masses of the plurality of known chemical structures;
(b) determining the mass of the unknown chemical structure;
(c) calculating mass differences between the mass of the unknown chemical structure and each of the known chemical structures;
(d) selecting a hypothetical substitutive structure;
(e) determining expected mass displacements caused by substitution of the hypothetical substitutive structure for each building block of each of the known chemical structures;
(f) determining the differences between the expected mass displacements determined in step (e);
(g) selecting a hypothetical additive structure;
(h) determining differences between the differences determined in step (f) and mass displacements caused by the addition of the hypothetical additive structure;
(i) of the differences identified in step (h), identifying an unknown chemical structure mass associated with the same number of differences as the sigma value for the predetermined number of building blocks;
(j) for the unknown chemical structure mass identified in step (i), identifying an associated known chemical structure; and
(k) for the associated known chemical structure identified in step (j), replacing two selected building blocks with the hypothetical substitutive structure and adding the hypothetical additive structure to form a hypothetical associated chemical structure, such that the mass of the associated known chemical structure equals the mass of the unknown chemical structure, said hypothetical associated chemical structure comprising the unknown chemical structure.

21. The method of claim 20 wherein the masses of the known and unknown chemical structures are obtained using mass spectrometry.

22. The method of claim 20 wherein step (c) comprises generating a mass difference table from the masses of the plurality of known chemical structures and the unknown chemical structure.

23. The method of claim 20 wherein said plurality of known chemical structures comprises a combinatorial library.

24. The method of claim 20 wherein at least some steps are implemented in a computer.

25. The method of claim 20 wherein steps (b), (c), (e), (f), (h) and (k) are implemented in a computer.

26. The method of claim 20 wherein steps (a)-(k) are implemented in a computer.

27. A method of identifying members of an undesired set of chemical structures expected to be structurally related to members of a desired set of chemical structures, comprising:
(a) identifying the members of the desired set and the masses of the members;
(b) determining the masses of the members of the undesired set;
(c) calculating mass differences between the members of the desired set;
(d) calculating mass differences between the members of the undesired set;
(e) ranking the mass differences found in step (c) in order of frequency;
(f) ranking the mass differences found in step (d) in order of frequency; and
(g) identifying members of the undesired set corresponding to mass differences having at least a given frequency if equal mass differences having at least a given frequency also exist for the desired set, said identified members of the undesired set expected to be structurally related to at least one member of the desired set.

28. The method of claim 27 further comprising:
(h) identifying hypothetical additive structures and corresponding mass displacements of the hypothetical additive structures;
(i) identifying mass differences identified in step (d) equal to any of the mass displacements; and
(j) identifying members of the undesired set corresponding to the mass differences identified in step (i) as expected to be structurally related to at least one member of the desired set.

29. The method of claim 27 further comprising:
(h) identifying hypothetical additive structures and corresponding mass displacements;
(i) adjusting mass differences calculated in step (c) by the mass displacements; and
(j) identifying members of the undesired set corresponding to adjusted mass differences having at least a given frequency if equal mass differences having at least a given frequency also exist for the desired set, said identified members of the undesired set expected to be structurally related to at least one member of the desired set.

30. The method of claim 29 wherein adjusting mass differences comprises subtracting the mass displacements from said mass differences.

31. The method of claim 29 wherein adjusting mass differences comprises subtracting the mass differences from said mass displacement.

32. The method of claim 27 wherein each member of the desired set comprises a core coupled with a predetermined number of building blocks, the method further comprising:
(h) selecting a hypothetical substitutive structure having a predetermined mass;
(i) calculating expected mass displacements caused by substitution of the hypothetical substitutive structure for each building block;
(j) calculating mass differences between the masses of the members of the desired set and members of the undesired sets;
(k) identifying expected mass displacements equal to mass differences calculated in step (j);
(l) of the expected mass displacements identified as being equal to a mass difference, identifying an undesired set mass associated with the same number of identified expected mass displacements as the predetermined number of building blocks; and
(m) reporting the undesired set mass found in step (1), the associated expected mass displacements, and the predetermined mass of the hypothetical substitutive structure.

33. The method of claim 32 further comprising incrementing the predetermined mass of the hypothetical substitutive structure, and repeating steps (i) through (m).

34. The method of claim 33 wherein the predetermined mass of the hypothetical substitutive structure is incremented until the predetermined mass of the hypothetical substitutive structure reaches a predetermined maximum value.

35. A computer program product in computer-readable media for use in identifying an unknown chemical structure having a mass related to at least one of a plurality of known chemical structures having masses, each of the known chemical structures comprising a core coupled with a predetermined number of building blocks, the computer program product comprising:
(a) means for calculating mass differences between the mass of the unknown chemical structure and each of the known chemical structures;
(b) means for determining expected mass displacements caused by substitution of a hypothetical substitutive structure for each building block of each of the known chemical structures;
(c) means for identifying expected mass displacements equal to a mass difference calculated by means (a);
(d) for the expected mass displacements identified as being equal to a mass difference, means for identifying an unknown chemical structure mass associated with the same number of identified expected mass displacements as the predetermined number of building blocks;
(e) for the unknown chemical structure mass identified by means (d), means for identifying an associated known chemical structure; and
(f) for the associated known chemical structure identified by means (e), means for replacing a selected building block with the hypothetical substitutive structure to form a hypothetical associated chemical structure, such that the mass of the associated known chemical structure equals the mass of the unknown chemical structure, said hypothetical associated chemical structure comprising the unknown chemical structure.

* * * * *